(12) United States Patent
Berry

(10) Patent No.: US 7,691,099 B2
(45) Date of Patent: Apr. 6, 2010

(54) DEUTERATED OCULAR SOLUTIONS FOR LTK AND OTHER SURGICAL EYE PROCEDURES

(75) Inventor: Michael J. Berry, Carmel, CA (US)

(73) Assignee: NTK Enterprises, Inc., Plano, TX (US)

( * ) Notice: Subject to any disclaimer, the term of this patent is extended or adjusted under 35 U.S.C. 154(b) by 17 days.

(21) Appl. No.: 11/825,816

(22) Filed: Jul. 9, 2007

(65) Prior Publication Data

US 2008/0027418 A1  Jan. 31, 2008

Related U.S. Application Data

(60) Provisional application No. 60/830,292, filed on Jul. 12, 2006.

(51) Int. Cl.
*A61B 18/20* (2006.01)
(52) U.S. Cl. ............................... 606/5; 606/4; 128/898
(58) Field of Classification Search ................ 606/4–6; 607/88–92; 128/898
See application file for complete search history.

(56) References Cited

U.S. PATENT DOCUMENTS

| | | | |
|---|---|---|---|
| 4,905,711 A * | 3/1990 | Bennett et al. ............ | 128/869 |
| 4,976,709 A | 12/1990 | Sand | |
| 5,129,895 A | 7/1992 | Vassiliadis et al. | |
| 5,137,530 A | 8/1992 | Sand | |
| 5,152,759 A | 10/1992 | Parel et al. | |
| 5,263,951 A | 11/1993 | Spears et al. | |
| 5,281,211 A | 1/1994 | Parel et al. | |
| 5,304,169 A | 4/1994 | Sand | |
| 5,334,190 A | 8/1994 | Seiler | |
| 5,344,418 A | 9/1994 | Ghaffari | |
| 5,348,551 A | 9/1994 | Spears et al. | |
| 5,374,265 A | 12/1994 | Sand | |
| 5,437,658 A | 8/1995 | Muller et al. | |

(Continued)

FOREIGN PATENT DOCUMENTS

WO  WO 92/01430  2/1992

(Continued)

OTHER PUBLICATIONS

Douglas D. Koch et al., "Intrastromal Procedures: The Use of the Noncontact Holmium:YAG Laser for Correction of Hyperopia-Sunrise Technologies Experience," Surgery for Hyperopia and Presbyopia, 1997, pp. 135-144.

(Continued)

*Primary Examiner*—Ahmed M Farah

(57) ABSTRACT

A deuterated ocular solution is applied to an eye. The deuterated ocular solution includes deuterated water and one or more ocular drugs (such as proparacaine). A protective corneal device is applied to a cornea of the eye. The device includes a window configured to contact at least a portion of the cornea. At least part of the cornea is irradiated using light energy that passes through the window during a cornea reshaping procedure, where the window is substantially transparent to the light energy. The window of the protective corneal device and the deuterated ocular solution may prevent clinically significant damage to a corneal epithelium of the cornea during the cornea reshaping procedure, such as by preventing a temperature of the corneal epithelium from exceeding approximately 70° C. during the cornea reshaping procedure. This may help to avoid a wound healing response in the eye and an associated regression of refractive correction.

10 Claims, 10 Drawing Sheets

U.S. PATENT DOCUMENTS

| | | | |
|---|---|---|---|
| 5,484,432 | A | 1/1996 | Sand |
| 5,591,157 | A | 1/1997 | Hennings et al. |
| 5,618,284 | A | 4/1997 | Sand |
| 5,649,922 | A | 7/1997 | Yavitz |
| 5,779,696 | A * | 7/1998 | Berry et al. .................. 606/16 |
| 5,810,801 | A | 9/1998 | Anderson et al. |
| 5,814,040 | A | 9/1998 | Nelson et al. |
| 5,820,624 | A | 10/1998 | Yavitz |
| 5,820,626 | A | 10/1998 | Baumgardner |
| 5,865,830 | A | 2/1999 | Parel et al. |
| 5,885,274 | A | 3/1999 | Fullmer et al. |
| 5,968,034 | A | 10/1999 | Fullmer et al. |
| RE36,634 | E | 3/2000 | Ghaffari |
| 6,033,396 | A | 3/2000 | Huang et al. |
| 6,079,861 | A | 6/2000 | Woodward et al. |
| 6,099,521 | A | 8/2000 | Shadduck |
| 6,120,497 | A | 9/2000 | Anderson et al. |
| 6,149,643 | A | 11/2000 | Herekar et al. |
| 6,159,205 | A | 12/2000 | Herekar et al. |
| 6,161,546 | A | 12/2000 | Yavitz |
| 6,162,210 | A | 12/2000 | Shadduck |
| 6,171,301 | B1 | 1/2001 | Nelson et al. |
| 6,200,308 | B1 | 3/2001 | Pope et al. |
| D441,080 | S | 4/2001 | Herekar et al. |
| 6,210,399 | B1 | 4/2001 | Parel et al. |
| 6,248,103 | B1 | 6/2001 | Tannenbaum et al. |
| 6,254,594 | B1 | 7/2001 | Berry |
| 6,312,450 | B1 * | 11/2001 | Yavitz et al. .................. 607/88 |
| 6,342,053 | B1 | 1/2002 | Berry |
| 6,413,253 | B1 | 7/2002 | Koop et al. |
| 6,451,007 | B1 | 9/2002 | Koop et al. |
| 6,514,244 | B2 | 2/2003 | Pope et al. |
| 6,520,956 | B1 | 2/2003 | Huang |
| 6,659,999 | B1 | 12/2003 | Anderson et al. |
| 6,679,855 | B2 | 1/2004 | Horn et al. |
| 6,736,806 | B2 | 5/2004 | Ruiz et al. |
| 7,189,225 | B2 * | 3/2007 | Rosen ........................... 606/6 |
| 2002/0099363 | A1 | 7/2002 | Woodward et al. |
| 2002/0143322 | A1 | 10/2002 | Haghighi |
| 2006/0287662 | A1 | 12/2006 | Berry et al. |

OTHER PUBLICATIONS

Liane Clamen Glazer et al., "Complications of Hyperopia and Presbyopia Surgery," Hyperopia and Presbyopia, 2003, pp. 291-313.
Stringer H. et al., "Shrinkage Temperature of Eye Collagen," Nature, vol. 204, No. 4965, Dec. 26, 1964, pp. 1307.
David Borja et al., "Kinetics of Corneal Thermal Shrinkage," Ophthalmic Technologies XIV, Proceeding of SPIE, vol. 5314, 2004, pp. 79-87.
Danny Y. Lin et al., "Two-Year Results of Conductive Keratoplasty for the Correction of Low to Moderate Hyperopia," Journal of Cataract and Refractive Surgery, vol. 29, No. 12, Dec. 2003, pp. 2339-2350.
Daniel G. Dawson, MD et al., "Long-Term Histopathologic Findings in Human Corneal Wounds After Refractive Surgical Procedures," American Journal of Ophthalmology, vol. 139, No. 1, Jan. 2005, pp. 168-178.
Renato Ambrosio et al., "Wound Healing After Hyperopic Corneal Surgery, Why is there greater regression in the treatment of hyperopia?," Custom LASIK: Surgical Techniques and Complications, pp. 645-654.
David Huang, MD, PhD et al., "Mathematical Model of Corneal Surface Smoothing After Laser Refractive Surgery," American Journal of Ophthalmology, vol. 135, No. 3, Mar. 2003, pp. 267-278.
Steven E. Wilson, MD, "Analysis of the Keratocyte Apoptosis, Keratocyte Proliferation, and Myofibroblast Transformation Responses After Photorefractive Keratectomy and Laser in SITU Keratomileusis," Transactions of the American Ophthalmological Society, vol. 100, 2002, pp. 411-433.
Brian M. Stramer et al., "Molecular Mechanisms Controlling the Fibrotic Repair Phenotype in Cornea: Implications for Surgical Outcomes," Investigative Ophthalmology and Visual Science, vol. 44, No. 10, Oct. 2003, pp. 4237-4246.
S.E. Wilson et al., "Myofibroblast Generation in the Anterior Stroma Is Triggered by Surface Irregularity,", Abstract of a paper presented at the Association for Research on Vision and Ophthalmology Annual Conference, Fort Lauderdale, FL, May 2, 2005, 1 page.
Russell L. McCally, PhD et al., "Cornea Epithelial Damage Thresholds in Rabbits Exposed to Tm: YAG Laser Radiation at 2.02 μm," Lasers in Surgery and Medicine, vol. 12, No. 6, Dec. 1992, pp. 598-603.
R. L. McCally et al., "Stromal Damage in Rabbit Corneas Exposed to $CO_2$ Laser Radiation," Experimental Eye Research, vol. 37, 1983, pp. 543-550.
Keith M. Meek et al., "The Organization of Collagen in the Corneal Stroma," Experimental Eye Research, vol. 78, No. 3, Mar. 2004, pp. 503-512.
Douglas D. Koch et al., "HF Chemical Laser Photothermal Keratoplasty," Investigative Ophthalmology and Visual Science, vol. 32, No. 4, Mar. 1991, pp. 994.
J. C. Allain et al., "Isometric Tensions Developed During The Hydrothermal Swelling of Rat Skin," Connective Tissue Research, vol. 7, No. 3, 1980, pp. 127-133.
G. L. Valderrama et al., "Temperature Distributions in Laser-Irradiated Tissues," Proceedings of Laser-Tissue Interaction II, vol. 1427, Jan. 21-23, 1991, pp. 200-213.
Brian P. Dempsey et al., "Cornea Heat Transfer," TRW Space and Technology Group, Aug. 27, 1990, 60 pages.
R. Mapstone, "Measurement of Corneal Temperature," Experimental Eye Research, 1968, pp. 237-243.
Ivar Horven, "Corneal Temperature in Normal Subjects and Arterial Occlusive Disease," Acta Ophthalmologica, vol. 53, 1975, pp. 863-874.
H. S. Carslaw et al., "Conduction of Heat in Solids," 2nd Edition, pp. 58-62.
Jukka A. O. Moilanen et al., "Long-Term Corneal Morphology After PRK By In Vivo Confocal Microscopy," Investigative Ophthalmology & Visual Science, Mar. 2003, vol. 44, No. 3, pp. 1064-1069.
Jianhua Wang et al., "Noncontact Measurements of Central Corneal Epithelial and Flap Thickness After Laser In Situ Keratomileusis," Investigative Ophthalmology & Visual Science, Jun. 2004, vol. 45, No. 6, pp. 1812-1816.
Gary Lask et al., "Nonablative Laser Treatment of Facial Rhytides," SPIE, vol. 2970, 1997, pp. 338-349.
Thomas E. Milner et al., "Analysis of Nonablative Skin Resurfacing," SPIE, vol. 2970, 1997, pp. 367-373.
T. Joshua Pfefer et al., "Bioheat Transfer Analysis of Cryogen Spray Cooling During Laser Treatment of Port Wine Stains," Lasers in Surgery and Medicine, 2000, pp. 145-157.
Walter G. Driscoll et al., "Handbook of Optics," Section 10, Polarization, 1978, 8 pages.
"Index of Refraction Values and Photonics Calculations," www.luxpop.com, 9 pages.
Notification of Transmittal of the International Search Report and the Written Opinion of the International Searching Authority, or the Declaration dated Aug. 8, 2008 in connection with PCT Application No. PCT/US07/15718.
Notification of Transmittal of the International Search Report and the Written Opinion of the International Searching Authority, or the Declaration dated Nov. 21, 2008 in connection with PCT Application No. PCT/US2008/073607.

* cited by examiner

DEUTERATED OCULAR SOLUTIONS FOR LTK AND OTHER SURGICAL EYE PROCEDURES

CROSS-REFERENCE TO RELATED APPLICATIONS

This application claims priority under 35 U.S.C. § 119(e) to U.S. Provisional Patent Application No. 60/830,292 filed on Jul. 12, 2006, which is hereby incorporated by reference.

This application is related to the following U.S. Patent Applications:

Ser. No. 60/684,749 entitled "DEVICE, SYSTEM, AND METHOD FOR CORNEA APPLANATION AND EPITHELIUM PROTECTION DURING CORNEA RESHAPING" filed on May 26, 2005;

Ser. No. 60/695,175 entitled "DEVICE, SYSTEM, AND METHOD FOR ENHANCED PROTECTION OF THE CORNEAL EPITHELIUM DURING CORNEA RESHAPING" filed on Jun. 29, 2005; and Ser. No. 11/440,794 entitled "DEVICE, SYSTEM, AND METHOD FOR EPITHELIUM PROTECTION DURING CORNEA RESHAPING" filed on May 25, 2006;

all of which are hereby incorporated by reference.

TECHNICAL FIELD

This disclosure is generally directed to ocular solutions. More specifically, this disclosure is directed to deuterated ocular solutions for laser thermal keratoplasty (LTK) and other surgical eye procedures.

BACKGROUND

Today, there are hundreds of millions of people in the United States and around the world who wear eyeglasses or contact lenses to correct ocular refractive errors. The most common ocular refractive errors include myopia (nearsightedness), hyperopia (farsightedness), astigmatism, and presbyopia.

Myopic vision can be modified, reduced, or corrected by flattening the cornea axisymmetrically around the visual axis to reduce its refractive power. Hyperopic vision can be modified, reduced, or corrected by steepening the cornea axisymmetrically around the visual axis to increase its refractive power. Regular astigmatic vision can be modified, reduced, or corrected by flattening or steepening the cornea with the correct cylindrical curvatures to compensate for refractive errors along various meridians. Irregular astigmatism often requires correction by a more complex refractive surgical procedure. Presbyopic vision can be modified, reduced, or corrected by rendering the cornea multifocal by changing its shape annularly so that one annular zone focuses distant rays of light properly while another annular zone focuses near rays of light properly.

There are various procedures that have been used to correct ocular refractive errors, such as laser thermal keratoplasty (LTK). LTK uses laser light to heat the cornea, causing portions of the cornea to shrink over time. For example, human corneal stromal collagen may shrink when heated to a temperature above approximately 55° C. The stroma is the central, thickest layer of the cornea. The stroma is formed mainly of keratocytes embedded in an extracellular matrix composed of collagen fibers, proteoglycans, water, and other materials. If the pattern of stromal collagen shrinkage is properly selected, the cornea is reshaped to reduce or eliminate one or more ocular refractive errors. LTK typically does not remove corneal tissue and does not penetrate the cornea physically with a needle or other device.

A problem with LTK and other procedures is regression of refractive correction, meaning the correction induced during a procedure is reduced or eliminated over time and an ocular refractive error returns. Corneal wound healing may be one cause of this regression, and a corneal wound healing response may be triggered by damage to the corneal epithelium in the cornea. The corneal epithelium can be damaged, for example, if it is heated to a temperature of approximately 70° C. or greater, even if only for a period of a few seconds or less.

Moreover, during reshaping of a cornea using LTK or another procedure, it may be desirable to use one or more ocular or ophthalmic solutions, such as a topical anesthetic. However, these ophthalmic solutions may often interfere with the LTK or other procedure, such as by interfering with the corneal reshaping.

SUMMARY

This disclosure provides deuterated ocular solutions for LTK and other surgical eye procedures.

In a first embodiment, a method includes applying a deuterated ocular solution to an eye. The eye includes a cornea, and the deuterated ocular solution includes deuterated water and one or more ocular drugs. The method also includes applying a device to the cornea of the eye, where the device includes a window configured to contact at least a portion of the cornea. The method further includes irradiating at least part of the cornea using light energy that passes through the window during a cornea reshaping procedure. The window is substantially transparent to the light energy.

In particular embodiments, the one or more ocular drugs include proparacaine.

In other particular embodiments, the method further includes preventing, using the window and the deuterated ocular solution, clinically significant damage to a corneal epithelium of the cornea during the cornea reshaping procedure. For example, the method could include preventing a temperature of the corneal epithelium from exceeding approximately 70° C. during the cornea reshaping procedure.

In a second embodiment, an apparatus includes a suction ring configured to attach the apparatus to an eye, where the eye includes a cornea. The apparatus also includes a window configured to contact at least a portion of the cornea. The window is substantially transparent to light energy that irradiates the cornea during a cornea reshaping procedure. The window is also configured to cool at least a portion of a corneal epithelium in the cornea during the cornea reshaping procedure. In addition, the apparatus includes a reservoir configured to hold a deuterated ocular solution. The deuterated ocular solution includes deuterated water and one or more ocular drugs and is for application to the eye before the cornea reshaping procedure.

In a third embodiment, a system includes a light source configured to generate light energy for a cornea reshaping procedure. The system also includes a device configured to be applied to an eye that includes a cornea. The device includes a window configured to contact at least a portion of the cornea. The window is substantially transparent to the light energy. The window is also configured to cool at least a portion of a corneal epithelium in the cornea during the cornea reshaping procedure. In addition, the system includes a container holding a deuterated ocular solution. The deuterated ocular solution includes deuterated water and one or more ocular drugs and is for application to the eye before the cornea reshaping procedure.

Other technical features may be readily apparent to one skilled in the art from the following figures, descriptions, and claims.

BRIEF DESCRIPTION OF THE DRAWINGS

For a more complete understanding of this disclosure and its features, reference is now made to the following description, taken in conjunction with the accompanying drawings, in which.

DETAILED DESCRIPTION

Figure 1:
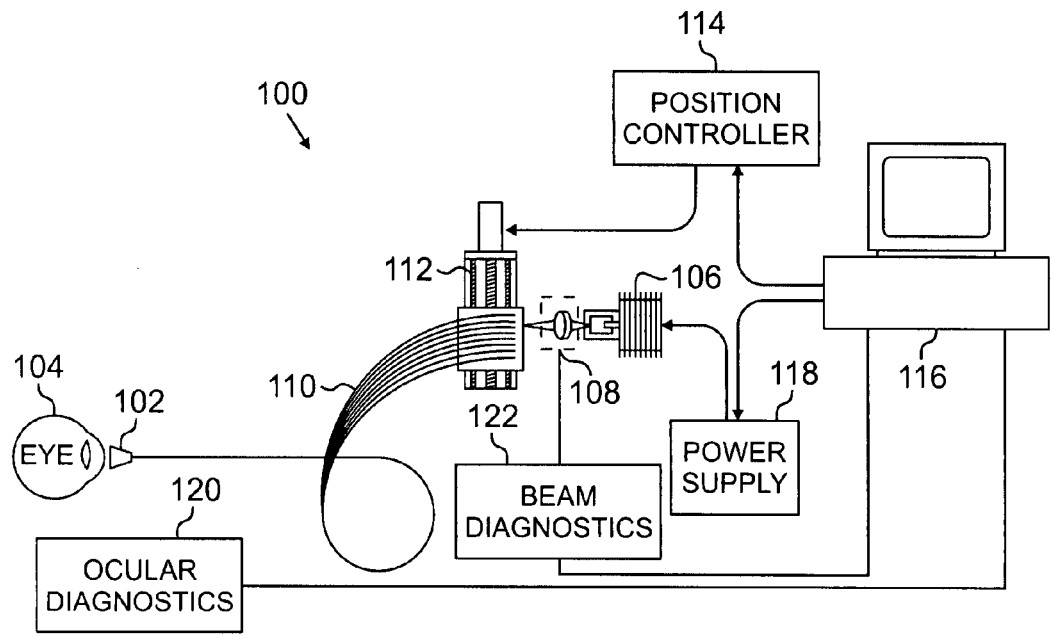
FIG. 1 illustrates an example system for cornea reshaping according to one embodiment of this disclosure.

FIG. 1 illustrates an example system 100 for cornea reshaping according to one embodiment of this disclosure. The embodiment of the system 100 shown in FIG. 1 is for illustration only. Other embodiments of the system 100 may be used without departing from the scope of this disclosure.

In this example, the system 100 includes a protective corneal applanator device 102. The protective corneal applanator device 102 is pressed against a patient's eye 104 during a cornea reshaping procedure. For example, the protective corneal applanator device 102 may be used during laser thermal keratoplasty (LTK) or other procedure meant to correct one or more ocular refractive errors in the patient's eye 104.

Figure 2:
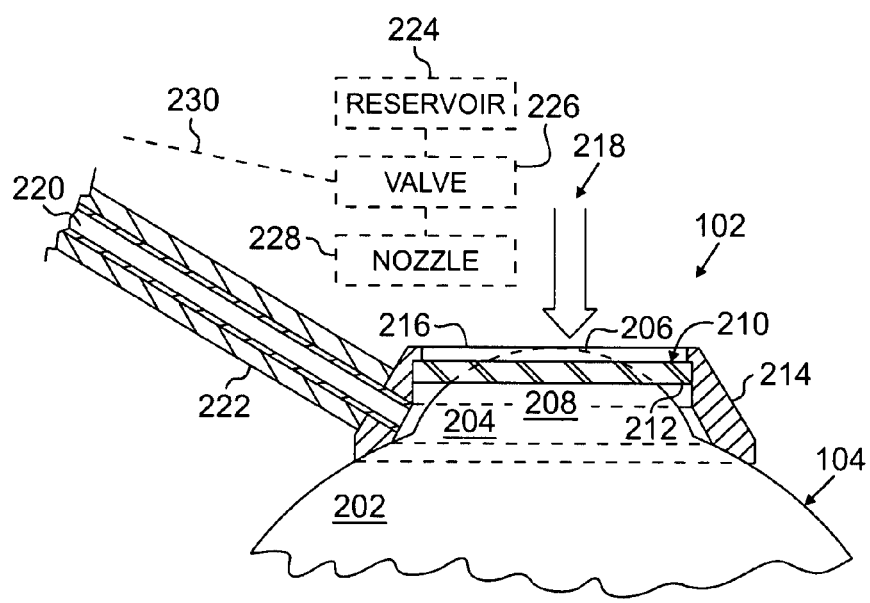
FIG. 2 illustrates an example protective corneal applanator device according to one embodiment of this disclosure.

Among other things, the protective corneal applanator device 102 helps to reduce or eliminate damage to the corneal epithelium of the patient's eye 104 during the cornea reshaping procedure. For example, the protective corneal applanator device 102 could act as a heat sink to conduct heat away from the patient's eye 104 during the procedure. This helps to reduce the temperature of the corneal epithelium, which may help to reduce or eliminate damage to the corneal epithelium and avoid a corneal wound healing response that could lead to regression of refractive correction. One example embodiment of the protective corneal applanator device 102 is shown in FIG. 2, which is described below. In this document, the phrase "cornea reshaping procedure" refers to any procedure involving a patient's eye 104 that results in a reshaping of the cornea in the eye 104, whether the reshaping occurs immediately or over time.

The system 100 also includes a laser 106. The laser 106 provides laser light that is used to irradiate the patient's eye 104 during the cornea reshaping procedure. The laser 106 represents any suitable laser capable of providing laser light for a cornea reshaping procedure. For example, the laser 106 could represent a continuous wave laser, such as a continuous wave hydrogen fluoride chemical laser or a continuous wave thulium fiber laser. In other embodiments, the laser 106 could represent a pulsed laser, such as a pulsed holmium:yttrium aluminum garnet (Ho:YAG) laser. Any other suitable laser or non-laser light source capable of providing suitable radiation for a cornea reshaping procedure could also be used in the system 100.

The laser light produced by the laser 106 is provided to a beam distribution system 108. The beam distribution system 108 focuses the laser light from the laser 106. For example, the beam distribution system 108 could include optics that focus the laser light from the laser 106 to control the geometry, dose, and irradiance level of the laser light as it is applied to the cornea of the patient's eye 104 during the cornea reshaping procedure. The beam distribution system 108 could also include a shutter for providing a correct exposure duration of the laser light. In addition, the beam distribution system 108 could include a beam splitting system for splitting the focused laser light into multiple beams (which may be referred to as "laser beams," "treatment beams," or "beamlets"). The beam distribution system 108 includes any suitable optics, shutters, splitters, or other or additional structures for generating one or more beams for a cornea reshaping procedure. Examples of the beam splitting system in the beam distribution system 108 are shown in FIGS. 9A through 9D, which are described below.

One or more beams from the beam distribution system 108 are transported to the protective corneal applanator device 102 using a fiber optic array 110. The fiber optic array 110 includes any suitable structure(s) for transporting one or multiple laser beams or other light energy to the protective corneal applanator device 102. The fiber optic array 110 could, for example, include multiple groups of fiber optic cables, such as groups containing four fiber optic cables each. The fiber optic array 110 could also include attenuators that rebalance fiber outputs so as to make up for differences in optical fiber transmission through the array 110.

A translation stage 112 moves the fiber optic array 110 so that laser light from the laser 106 enters different ones of the fiber optic cables in the fiber optic array 110. For example, the beam distribution system 108 could produce four laser beams, and the translation stage 112 could move the fiber optic array 110 so that the four beams enter different groups of four fiber optic cables. Different fiber optic cables could deliver laser light onto different areas of the cornea in the patient's eye 104. The translation stage 112 allows the different areas of the cornea to be irradiated by controlling which fiber optic cables are used to transport the laser beams from the beam distribution system 108 to the protective corneal applanator device 102. The translation stage 112 includes any suitable structure for moving a fiber optic array. While the use of four laser beams and groups of four fiber optic cables has been described, any suitable number of laser beams and any suitable number of fiber optic cables could be used in the system 100.

A position controller 114 controls the operation of the translation stage 112. For example, the position controller 114 could cause the translation stage 112 to translate, thereby repositioning the fiber optic array 110 so that the laser beams from the beam distribution system 108 enter a different set of fiber optic cables in the array 110. The position controller 114 includes any hardware, software, firmware, or combination thereof for controlling the positioning of a fiber optic array.

A controller 116 controls the overall operation of the system 100. For example, the controller 116 could ensure that the system 100 provides predetermined patterns and doses of laser light onto the anterior surface of the cornea in the patient's eye 104. This allows the controller 116 to ensure that an LTK or other procedure is carried out properly on the patient's eye 104. In some embodiments, the controller 116 includes all of the controls necessary for a surgeon or other physician to have complete control of the cornea reshaping procedure, including suitable displays of operating variables showing what parameters have been preselected and what parameters have actually been used. As a particular example, the controller 116 could allow a surgeon to select, approve of, or monitor a pattern of irradiation of the patient's eye 104. If a pulsed laser 106 is used, the controller 116 could also allow the surgeon to select, approve of, or monitor the pulse duration, the number of pulses to be delivered, the number of pulses actually delivered to a particular location on the patient's eye 104, and the irradiance of each pulse. In addition, the controller 116 may synchronize the actions of various components in the system 100 to obtain accurate delivery of laser light onto the cornea of the patient's eye 104. The controller 116 includes any hardware, software, firmware, or combination thereof for controlling the operation of the system 100. As an example, the controller 116 could represent a computer (such as a desktop or laptop computer) at a surgeon's location capable of displaying elements of the cornea reshaping procedure that are or may be of interest to the surgeon.

A power supply 118 provides power to the laser 106. The power supply 118 is also controlled by the controller 116. This allows the controller 116 to control if and when power is provided to the laser 106. The power supply 118 represents any suitable source(s) of power for the laser 106.

As shown in FIG. 1, the system 100 also includes one or more ocular diagnostic tools 120. The ocular diagnostic tools 120 may be used to monitor the condition of the patient's eye 104 before, during, or after the cornea reshaping procedure. For example, the ocular diagnostic tools 120 could include a keratometer or other corneal topography measuring device, which is used to measure the shape of the cornea in the patient's eye 104. By comparing the shape of the cornea before and after the procedure, this tool may be used to determine a change in the shape of the cornea. After treatment, keratometric measurements may be performed to produce corneal topographic maps that verify the desired correction has been obtained. In some embodiments, the keratometer may provide a digitized output from which a visual display is producible to show the anterior surface shape of the cornea 204. As another example, the ocular diagnostic tools 120 could include a mechanism for viewing the cornea in the patient's eye 104 during the procedure, such as a surgical microscope or a slit-lamp biomicroscope. Any other or additional ocular diagnostic tools 120 could be used in the system 100.

In addition, the system 100 may include a beam diagnostic tool 122. The beam distribution system 108 could include a beam splitter that samples a small portion (such as a few percent) of one or more laser beams. A sampled laser beam could represent the beam that is to be split or one of the beams after splitting. The sampled portion of the beam is directed to the beam diagnostic tool 122, which measures laser beam parameters such as power, spot size, and irradiance distribution. In this way, the controller 116 can verify whether the patient's eye 104 is receiving a proper amount of laser light and whether various components in the system 100 are operating properly.

In one aspect of operation, a patient may lie down on a table that includes a head mount for accurate positioning of the patient's head. The protective corneal applanator device 102 may be attached to an articulated arm that holds the device 102 in place. The articulated arm may be attached to a stable platform, thereby helping to restrain the patient's eye 104 in place when the protective corneal applanator device 102 is attached to the patient's eye 104. The patient may look up toward the ceiling during the procedure, and the laser beams transported by the fiber optic array 110 may be directed vertically downward onto the patient's eye 104. Other procedures may vary from this example. For example, the protective corneal applanator device 102 may have a small permanent magnet mounted on the center of its front surface. This magnet may be used to attach and centrate a fiber optic holder shaft on the protective corneal applanator device 102 using another small permanent magnet that is mounted on the fiber optic holder shaft. In addition, as described in more detail below, one or more deuterated ocular/ophthalmic solutions can be used during the procedure.

A surgeon or other physician who performs the cornea reshaping procedure may use a tool (such as an ophthalmic surgical microscope, a slit-lamp biomicroscope, or other tool 120), together with one or more visible tracer laser beams (from a low energy visible laser such as a helium-neon laser) collinear with the treatment beams, to verify the proper positioning of the treatment beams. The surgeon or other physician also uses the controller 116 to control the system 100 so as to produce the correct pattern, irradiance, and exposure duration of the treatment beams. The controller 116 could be used by the surgeon or other physician as the focal point for controlling all variables and components in the system 100. During the procedure, the laser 106 produces functionally effective laser light, which is processed to produce the correct pattern and dose of functionally effective light on the anterior surface of the cornea in the patient's eye 104.

As described in more detail below, the protective corneal applanator device 102 provides various features or performs various functions during the cornea reshaping procedure. Among other things, the protective corneal applanator device 102 helps to provide thermal protection for the corneal epithelium in the cornea of the patient's eye 104 during the procedure. For example, the protective corneal applanator device 102 may conduct heat away from the cornea in the patient's eye 104 during the procedure. This may help to reduce the temperature of the corneal epithelium in the patient's eye 104. By reducing the temperature of the corneal epithelium during the procedure, the protective corneal applanator device 102 may help to prevent the corneal epithelium from reaching a threshold temperature at which clinically significant damage to the corneal epithelium occurs. The threshold temperature could, for example, occur at approximately 70° C. By keeping the corneal epithelium below this threshold temperature, clinically significant damage to the corneal epithelium may be avoided. In this document, the phrase "clinically significant damage" refers to damage that triggers a sufficient corneal wound healing that leads to significant regression of refractive correction. Although some damage may be inherent in particular embodiments, clinically insignificant damage would not trigger a sufficient corneal wound healing and is therefore acceptable.

In some embodiments, the reshaping procedure produces ocular changes in the stroma of the eye 104 without inducing clinically significant damage to the viability of ocular structures. Although some damage may be inherent in particular embodiments, clinically insignificant damage means that the eye 104 continues to function optically and that the cellular layers continue to live and regenerate. For example, normal undamaged corneal stroma contains keratocytes, which are specialized cells that maintain stromal integrity and health by synthesizing collagen and proteoglycans (among other things). These "quiescent" keratocytes can be activated and transformed into repair phenotypes (fibroblasts and myofibroblasts) if triggered by, for example, significant damage to the epithelial basement membrane by corneal wounding. The repair phenotypes secrete collagenase to degrade damaged collagen, synthesize new collagen, and cause stromal remodeling (among other things). Clinically insignificant damage may not include a fibrotic wound healing response, including activation and transformation of keratocytes into their repair phenotypes, which leads to regression of refractive correction.

In this example, heating the collagen of the stroma to a temperature of at least 55 to 58° C. and up to a maximum of about 80° C. causes the collagen to shrink, thereby changing the shape of the cornea of the eye 104. The main structural change occurring during collagen shrinkage may be denaturation by a helix-coil phase transition in which Type I collagen molecules rearrange from a triple helix conformation to a random coil form due to the breakage of hydrogen bonds that maintain the triple helix. Other structural changes to the extracellular matrix may also be caused by heating. For example, the proteoglycans and the hydration state of the stroma may be changed, thereby contributing to corneal reshaping. In some embodiments, the maximum temperature of photothermal modification of the stroma could be restricted to approximately 75° C., the approximate threshold temperature for stromal keratocyte damage and necrosis, in order to reduce the possibility of clinically significant damage that leads to corneal wound healing responses and regression of refractive correction.

In these embodiments, the heating process can be caused by directing light energy onto the cornea of the eye 104 to cause absorption of the energy, which heats the stroma to the desired temperature. This may be done by providing a light source (such as laser 106) that radiates light energy characteristically deposited within a specified range of depths of the corneal tissue. In particular embodiments, for photothermal keratoplasty, wavelengths of light energy that are absorbed primarily within the anterior region (approximately one-third to one-half the thickness) of the cornea may be used.

The selection and control of the source of light energy that induces the thermal changes to the cornea of the eye 104 may be important. The variables used to select the appropriate amount and type of light energy may include wavelength, irradiance level, and time (duration). These three variables may be selected so that the amount of light energy is functionally effective to produce a predetermined change in the anterior portion only of the stroma. The light source can be a laser or a non-laser light source providing radiation of the appropriate wavelengths, irradiances, and durations to be absorbed within the stroma without penetrating deeply into the eye 104 in a manner that can damage the endothelium of the cornea or other structures of the eye 104. Additionally, the light source may accomplish the desired modification of the stroma by photothermal keratoplasty on a timescale in which thermal diffusion from the heated stroma into adjacent tissue does not damage the endothelium or other ocular structures. The light energy may also be of a type that can be directed onto the cornea and controlled to produce the appropriate thermal changes.

The following represents particular examples of lasers 106 that could be used in the system 100. The use of these particular examples does not limit the light energy source, preferred wavelength, irradiance, or duration of exposure in any way. As examples, thulium based lasers producing light within a wavelength range of approximately 1.8 to 2.1 microns can be effectively used. Thulium based lasers include a Tm:YAG laser (in which thulium ions are doped into a crystalline matrix of yttrium aluminum garnet) or a thulium fiber laser (in which thulium ions are doped into a glass fiber matrix). Hydrogen fluoride chemical lasers could also be used. In the following description, the term "wavelength" generally includes wavelengths of slightly greater and slightly smaller value and is often described in this disclosure as "one or more wavelengths."

In particular embodiments, the wavelength range of light energy from the laser 106 is about 2.4 microns to about 2.67 microns, such as approximately 2.5 to approximately 2.6 microns, for a hydrogen fluoride chemical laser. Light within this range of wavelengths is absorbed primarily in the anterior of the stroma. In other particular embodiments, light having wavelengths of 1.4 to 1.6, 1.8 to 2.2, and 3.8 to 7.0 microns may also be utilized. In yet other embodiments, any light having wavelengths that are absorbed with a penetration depth (i.e. 1/e attenuation depth) of 50 to 200 microns within the cornea of the eye 104 may be used. Since human corneas are typically 500 microns or more in thickness, the initial absorption of light energy at these wavelengths may not heat the corneal endothelium significantly, thus preventing damage to this vulnerable structure. By controlling the duration and irradiance level of light emitted at these wavelengths, substantial thermal diffusion of the absorbed light energy into adjacent tissue can be reduced or prevented so that thermal diffusion does not damage the corneal endothelium.

In some embodiments, the light source is a hydrogen fluoride light source, such as a hydrogen fluoride chemical laser that is tuned to produce only those wavelengths of hydrogen fluoride chemical laser radiation that are primarily absorbed in the first 50 to 200 microns of the anterior region of the cornea. The wavelengths characteristically emitted by a hydrogen fluoride chemical laser system typically fall within the range of about 2.4 microns to about 3.1 microns. An example of one light source that can be utilized is a modified Helios hydrogen fluoride mini-laser from Helios Inc., Longmont, Colo. This modified laser system uses special resonator optics that are designed to allow laser action on certain hydrogen fluoride wavelengths while suppressing all other wavelengths.

In some embodiments, the duration of exposure of the cornea to or time for application of the light energy is less than about one second. For example, the exposure time could range from about 10 ms to about 200 ms. The light energy may be applied in an intermittent or pulse form, with each pulse being less than one second. The level of irradiance may be selected to be a level wherein absorption is substantially linear. For example, the irradiance level (given in units of $W/cm^2$) may be less than $1 \times 10^5$ $W/cm^2$.

The variables of wavelength, duration, and irradiance may be highly interdependent. These variables may be interrelated in a way that a functional amount of light is delivered to the cornea of the eye 104 to make the desired predetermined physical changes in the curvature of the cornea without eliciting a wound healing response. One example interrelationship of variables includes wavelengths of 2.4 to 2.67 microns, a duration of less than one second, and an irradiance level of less than $1 \times 10^5$ W/cm$^2$.

Although FIG. 1 illustrates one example of a system 100 for cornea reshaping, various changes may be made to FIG. 1. For example, FIG. 1 illustrates one example system in which certain components (such as the protective corneal applanator device 102 and the beam splitting system in the beam distribution system 108) could be used. These components could be used in any other suitable system. Also, FIG. 1 illustrates a system for irradiating a patient's eye 104 using multiple laser beams transported over a fiber optic array 110. In other embodiments, the system 100 could generate any number of laser beams (including a single laser beam) for irradiating the patient's eye 104. In addition, various components in FIG. 1 could be combined or omitted and additional components could be added according to particular needs, such as by combining the controllers 114, 116 into a single functional unit.

FIG. 2 illustrates an example protective corneal applanator device 102 according to one embodiment of this disclosure. The embodiment of the protective corneal applanator device 102 shown in FIG. 2 is for illustration only. Other embodiments of the protective corneal applanator device 102 may be used without departing from the scope of this disclosure. Also, for ease of explanation, the protective corneal applanator device 102 may be described as operating in the system 100 of FIG. 1. The protective corneal applanator device 102 could be used in any other suitable system.

As shown in FIG. 2, the patient's eye 104 includes a sclera 202 and a cornea 204. The cornea 204 includes an outer or anterior surface 206 and a central optical zone 208. The central optical zone 208 represents the portion of the cornea 204 that is critical to the patient's eyesight. The central optical zone 208 may be defined, for example, by the diameter of the pupil in the eye 104. Typically, pupil diameter varies from patient to patient, varies based on different illumination levels, and decreases as a function of age. A typical pupil diameter (and hence the portion of the central optical zone 208) used for daylight vision may be 2 mm to 5 mm in diameter for adults. A typical pupil diameter used for lower illumination (mesoptic to scotopic) conditions may be larger (up to 6 mm or 7 mm) in diameter for adults. It may be desirable to maintain a clear central optical zone, free from significant optical aberrations that distort refraction, in order to achieve a high quality of vision under all illumination conditions.

The protective corneal applanator device 102 is removably attached to the anterior surface 206 of the cornea 204. In this example, the protective corneal applanator device 102 includes a transparent window 210 having a corneal engaging surface 212, a suction ring 214, and a focusing and centration aid and mask 216.

The transparent window 210 contacts the anterior surface 206 of the cornea 204 along the corneal engaging surface 212. The corneal engaging surface 212 acts as an interface between the protective corneal applanator device 102 and the cornea 204. The transparent window 210 is substantially transparent to light energy 218 (such as one or more laser beams from the beam distribution system 108) used to reshape the cornea 204. As described in more detail below, the transparent window 210 may, among other things, act as a heat sink to conduct heat away from the anterior or outer portion of the cornea 204 during a cornea reshaping procedure. The transparent window 210 may be made from any suitable material or combination of materials, such as sapphire, infrasil quartz, calcium fluoride, or diamond. The window 210 may also have any suitable thickness or thicknesses, such as a thickness of at least 0.5 mm. Also, an anti-reflection coating may be placed on at least part of the anterior surface of the transparent window 210 to minimize reflection loss at the air/window interface.

The suction ring 214 maintains the protective corneal applanator device 102 in place on the patient's eye 104 during the cornea reshaping procedure. For example, a vacuum port 220 could be used to produce suction along the suction ring 214, which holds the protective corneal applanator device 102 against the patient's eye 104. In some embodiments, the suction ring 214 is sized to encompass all or a substantial portion of the cornea 204. The suction ring 214 includes any suitable structure for maintaining the protective corneal applanator device 102 in place using suction. As an example, the suction ring 214 may be fabricated from a biocompatible and sterilizable material (such as a metal like titanium). As another example, the suction ring 214 may be fabricated from a biocompatible and disposable material (such as a plastic like polymethylmethacrylate). Also, the transparent window 210 may be mounted on the top surface of the suction ring 214 and bonded to the suction ring 214 to maintain a vacuum-tight seal.

The focusing and centration aid and mask 216 provides various guide and protection features during the cornea reshaping procedure. For example, the focusing and centration aid and mask 216 could provide a focusing and centration aid for accurate delivery of the light energy 218. The focusing and centration aid and mask 216 could also protect the central optical zone 208 of the cornea 204. As an example, the focusing and centration aid and mask 216 could reflect, absorb, or scatter the light energy 218 so that the light energy 218 is not directly transmitted into the central optical zone 208 of the cornea 204. In this way, the focusing and centration aid and mask 216 provides protection for regions of the anterior surface 206 of the cornea 204 that are not intended to be treated with the light energy 218. By avoiding damage to the central optical zone 208, the possibility of long-term, irreversible damage to vision may be reduced or avoided. The focusing and centration aid and mask 216 includes any suitable structure for guiding treatment or protecting portions of the patient's eye 104. The focusing and centration aid and mask 216 could, for example, include a metallic coating, an etched surface, or a reticle for positioning of light energy accurately on specified portions of the cornea 204. In some embodiments, the focusing and centration aid and mask 216 may be used in combination with focus lasers.

In other embodiments, the focusing and centration aid and mask 216 may include a small permanent magnet (such as a 3 mm diameter, 1.5 mm thick neodymium-iron-boron (NdFeB) magnet) that is mounted on the front surface of the transparent window 210. A second small permanent magnet may then be mounted in a fiber optic holder shaft (such as is shown in FIG. 3B) in order to attach a fiber optic array onto the transparent window 210 to provide accurate focusing and centration.

As shown in FIG. 2, the protective corneal applanator device 102 is attached to a positioning arm 222. The positioning arm 222 may be coupled to an articulated arm that is mounted on a secure surface. A surgeon or other physician may view the patient's eye 104 through the transparent window 210 of the protective corneal applanator device 102, and the surgeon or other physician may move the positioning arm 222 to place the device 102 onto the patient's eye 104. This could be done, for example, with the patient looking up toward the ceiling and with a light (such as a good background light) illuminating the protective corneal applanator device 102 and its surroundings. As a particular example, the surgeon or other physician can position the protective corneal applanator device 102 so that the focusing and centration aid and mask 216 is centered on the patient's pupil or the patient's line of sight (using a fixation light source). While FIG. 2 shows the vacuum port 220 residing within the positioning arm 222, the vacuum port 220 could be located elsewhere, such as directly on the suction ring 214.

The protective corneal applanator device 102 provides various features or performs various functions during a cornea reshaping procedure. For example, the protective corneal applanator device 102 may be used to provide a positioner/restrainer for accurate positioning of the light energy 218 on the anterior surface 206 of the cornea 204 and for restricting eye movement during the treatment. Also, the transparent window 210 may be substantially transparent to the light energy 218, allowing the light energy 218 to properly irradiate the cornea 204. The protective corneal applanator device 102 could also act as a thermostat to control the initial corneal temperature prior to irradiation. Further, the transparent window 210 may be sufficiently rigid to act as an applanator or a template for the cornea 204, allowing the transparent window 210 to alter the shape of the cornea 204 during the procedure. Moreover, the transparent window 210 could provide corneal hydration control during the procedure by restricting the tear film to a thin layer between the epithelium and the transparent window 210 and by preventing evaporation of water from the anterior cornea. Beyond that, the transparent window 210 could act as a heat sink with heat transfer properties suitable to cool the corneal epithelium during the cornea reshaping procedure and to prevent heating of the corneal epithelium to temperatures above a threshold damage temperature. In addition, the transparent window 210 could act as a substrate for depositing, etching, or otherwise fabricating patterns of absorbing, reflecting, or scattering surface areas of the focusing and centration aid and mask 216. This supports accurate delivery of the light energy 218, provides a pattern of light energy treatment, and protects the central optical zone 208 of the cornea 204. Depending on the implementation, the protective corneal applanator device 102 could provide one, some, or all of these features or functions.

The heat sink and thermostat functions of the protective corneal applanator device 102 may be used to maintain the corneal epithelium (such as an epithelial basement membrane of the epithelium) at a sufficiently cool temperature to prevent clinically significant damage to the epithelium. The epithelial basement membrane inhibits the transmission of cytokines such as TGF-β2 from the epithelium into the stroma, which is the central and thickest layer of the cornea 204. These cytokines may be inhibited to prevent the triggering of a fibrotic wound healing response in the stroma. Protection of the corneal epithelium may also reduce discomfort (due to pain, tearing, foreign body sensation, and photophobia) that a patient feels following the cornea reshaping procedure.

The protective corneal applanator device 102 may function as a thermostat by maintaining the initial temperature of the anterior surface 206 of the cornea 204 at a desired temperature before the procedure begins. As a particular example, the transparent window 210 of the protective corneal applanator device 102 may typically be at room temperature (such as approximately 20° C.), so the anterior surface 206 of the cornea 204 may be held at or near room temperature rather than at its normal physiological temperature (which may range from approximately 33° C. to 36° C.). In this way, the transparent window 210 may be used to provide initial cooling of the cornea, as well as accurate and reproducible temperature control, prior to the procedure. During the procedure, the protective corneal applanator device 102 may function as a heat sink to conduct heat caused by the light energy 218 away from the anterior surface 206 of the cornea 204. The initial cooling to room temperature (or a lower temperature with the aid of, for example, an active cooling technique as described below) may improve the efficacy of protection of the corneal epithelium from thermal damage.

In this example, the protective corneal applanator device 102 provides a passive heat sink function (where the transparent window 210 passively conducts heat away from the cornea 204). However, other techniques could be used to cool the cornea 204. For example, one or more active cooling techniques could be used, such as by cooling the window 210 using a steady-state refrigerator (such as a Peltier cooler). As another example, dynamic cooling could be used to cool the transparent window 210 prior to and during treatment. As shown in FIG. 2, a reservoir 224 could contain a liquid. The liquid could be extremely cold, such as liquid nitrogen or a cryogenic liquid (such as a fluorocarbon that is transparent to laser wavelengths). A valve 226 may open and close to selectively release the liquid from the reservoir 224. A nozzle 228 sprays the released liquid onto the transparent window 210, which may cool the transparent window 210 and allow the transparent window 210 to cool the cornea 204 more effectively. In some embodiments, the valve 226 is controlled automatically (such as by the controller 116) using one or more control signal lines 230. In particular embodiments, the nozzle 228 and possibly the valve 226 and reservoir 224 are integrated into the protective corneal applanator device 102. In other particular embodiments, the reservoir 224, valve 226, and nozzle 228 represent a separate component, such as a component that is held and operated by a surgeon or other physician or that is mounted separately from the protective corneal applanator device 102. The use of an active or dynamic cooling technique may decrease the thermal damage produced during the procedure, such as the thermal damage produced by several pulses of laser light during a pulsed Ho:YAG LTK treatment.

As described in more detail below, one or more deuterated ocular/ophthalmic solutions can also be used during a surgical eye procedure. In these embodiments, the reservoir 224 could contain a deuterated solution, the valve 226 may open and close to selectively release the deuterated solution from the reservoir 224, and the nozzle 228 sprays the released deuterated solution onto the patient's eye. This can be done before the transparent window 210 is placed onto the patient's eye. Again, the nozzle 228 and possibly the valve 226 and reservoir 224 could be integrated into the protective corneal applanator device 102, or these components could represent a separate component. Also, multiple ones of these components could be used, such as when a deuterated solution and active cooling are used during the surgical eye procedure. As one alternative, the deuterated solution may be instilled in droplet form into the patient's eye, and the patient can close his or her eyelids to permit the solution to take effect.

The applanation or template functions of the protective corneal applanator device 102 may be used to alter the shape of the cornea 204 for treatment. The applanation or template functions may be performed by the corneal engaging surface 212 of the transparent window 210. The applanation may be full or partial. For example, as shown in FIG. 2, the corneal engaging surface 212 is planar (i.e. completely flat). The transparent window 210 therefore fully applanates or flattens the portion of the cornea 204 contacted by the window 210, providing a reference plane for irradiation. In other embodiments, the transparent window 210 has a curved concave corneal engaging surface 212 that only partially applanates the portion of the cornea 204 contacted by the window 210. In particular embodiments, the curved concave corneal engaging surface 212 has a radius of curvature or radii of curvature greater than that of the cornea 204. Multiple radii of curvature may facilitate the production of an aspheric corneal shape that produces annular zones with different refractions. For example, a more prolate aspheric shape (compared to a normal cornea) may provide both fine distance and fine near visual acuities to patients who are presbyopic. In other particular embodiments, the curved concave corneal engaging surface 212 has a radius of curvature or radii of curvature substantially equal to the desired final corneal curvature(s) of the cornea 204. In this last case, the transparent window 210 acts as a template to facilitate production of the desired reshaped corneal surface.

The hydration control function of the protective corneal applanator device 102 is supported by the presence of the corneal engaging surface 212 against the anterior surface 206 of the cornea 204, which helps to reduce or prevent fluid evaporation from the cornea 204. Also, protection of the corneal epithelium from damage helps to prevent loss of hydration control associated with the normal (undamaged) epithelium. In some embodiments, a film of tears or ophthalmic solution may be placed between the transparent window 210 and the cornea 204, and a portion of this film may be squeezed out by application of the device 102 to the cornea 204 so that a thin, uniform thickness film remains. In particular embodiments, only one drop or a limited number of drops of anesthetic are applied prior to LTK or other treatment, and little or no solutions are used after treatment. In these embodiments, reducing the number and amount of ophthalmic solutions may be beneficial since the ophthalmic solutions may have adverse effects (including corneal wounding).

These elements of fluid control (providing a thin layer of fluid between the cornea 204 and the transparent window 210, limiting evaporation, and protecting against epithelial damage that leads to fluid redistribution) may provide accurate and reproducible dosimetry and action of light energy irradiation. This is because the amount of light energy 218 absorbed and its effects on corneal tissue are both functions of the hydration state of the cornea 204. In particular, film thickness and epithelial and stromal hydration affect the dosimetry of light irradiation of the cornea 204 since the film can absorb some of the incident light and the absorption coefficient and other physical properties of the cornea 204 are dependent on epithelial and stromal hydration.

The masking function of the protective corneal applanator device 102 may be performed by blocking most or all light energy 218 from irradiating the central optical zone 208 of the cornea 204. This helps to prevent inadvertent irradiation of the central optical zone 208. Also, the specific geometry of the pattern of the masking feature of the protective corneal applanator device 102 may be important to the corneal reshaping method. Different corrections and different degrees of correction can be encompassed within a single device 102 using interchangeable or interusable focusing and centration aids and masks 216. In some embodiments, the mask is found on the surface of the transparent window 210 opposite the corneal engaging surface 212, although the corneal engaging surface 212 itself may be used for masking purposes. In other embodiments, the mask can be located on a separate interchangeable window or mount that can be placed over the transparent window 210. In this way, controls are provided to reduce or eliminate risks to the patient. The central optical zone 208, the only zone critical to eyesight, may be untouched by the light energy 218. The viability of the corneal endothelium, a delicate and critical layer to human eyesight, together with other essential visual components of the eye 104, is maintained throughout the procedure.

In general, the protective corneal applanator device 102 may be used in combination with any noninvasive ophthalmological procedure for reshaping the anterior surface 206 of the cornea 204 in order to achieve a desired final refractive state such as emmetropia (normal distance vision of 20/20 on a Snellen visual acuity chart). The reshaping procedure uses a source of light energy 218 emitting a wavelength or wavelengths with correct optical penetration depths (i.e. 1/e attenuation depths) to induce thermal changes in the corneal stroma without damaging the viability of the corneal endothelium or the anterior surface 206 of the cornea 204 and without causing a significant corneal wound healing response that might lead to significant regression of corneal reshaping. Although the reshaping procedure is described as being performed only one time, repeated applications of the reshaping procedure may be desirable or necessary.

Although FIG. 2 illustrates one example of a protective corneal applanator device 102, various changes may be made to FIG. 2. For example, the components 224-230 could be omitted in the device 102. Also, the focusing and centration aid and mask 216 could be integrated with the transparent window 210. In addition, the focusing and centration aid and mask 216 could include a small permanent magnet mounted on the transparent window 210 that engages another small permanent magnet mounted in a fiber optic holder shaft (as shown in FIG. 3B).

Figure 3A:
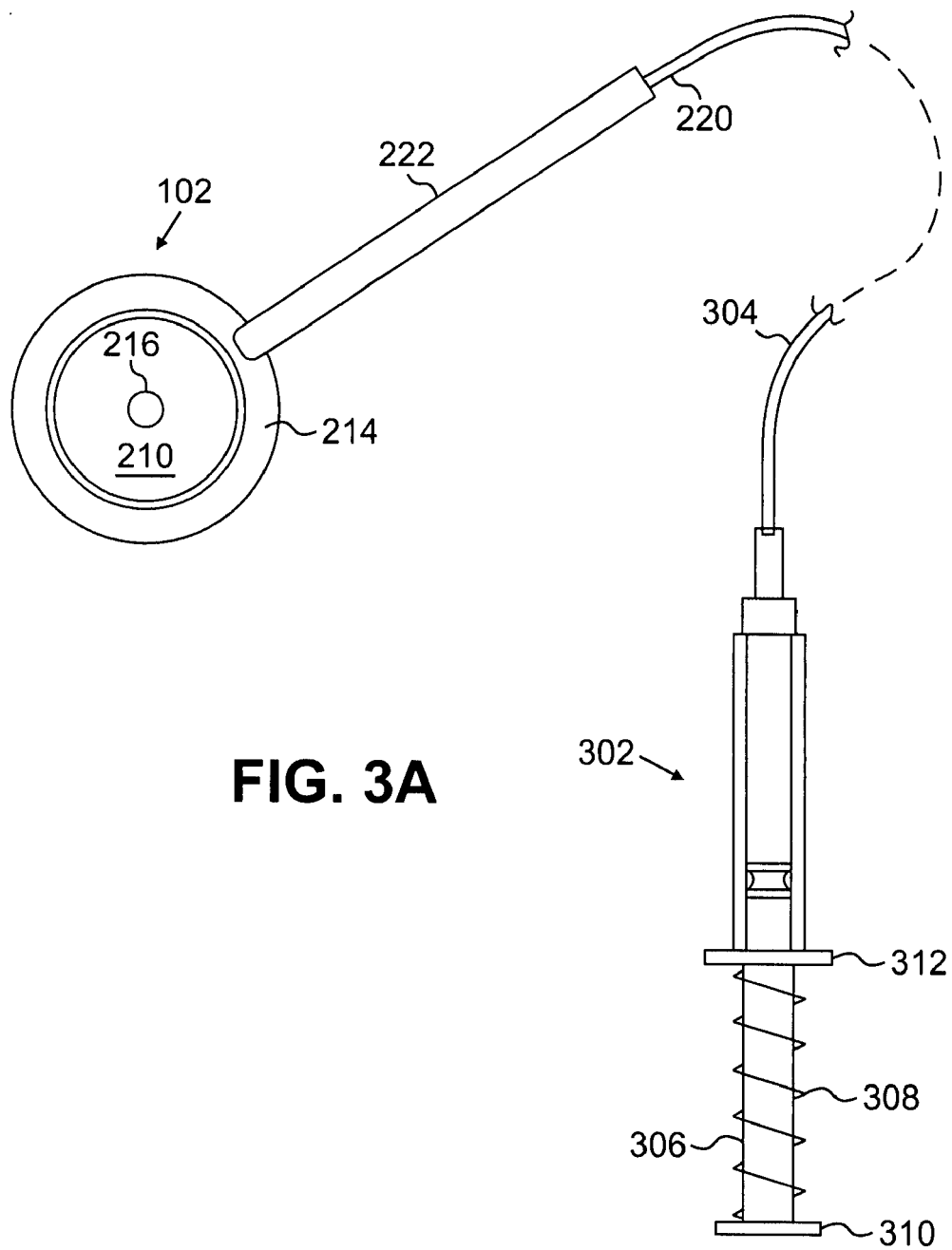
FIGS. 3A and 3B illustrate example uses of a protective corneal applanator device according to one embodiment of this disclosure.
Figure 3B:
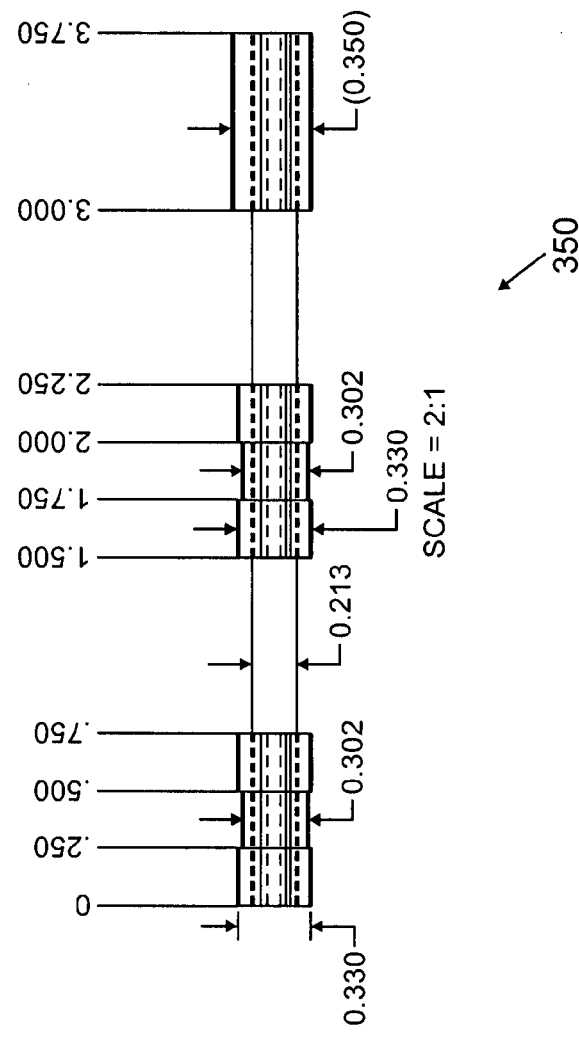
Figure 3B:
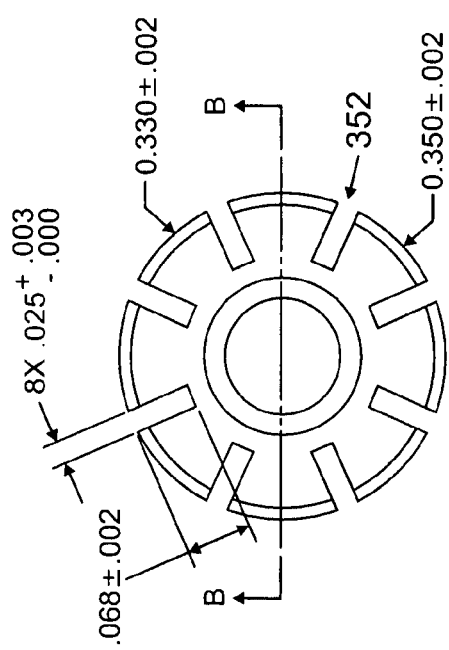
Figure 3B:
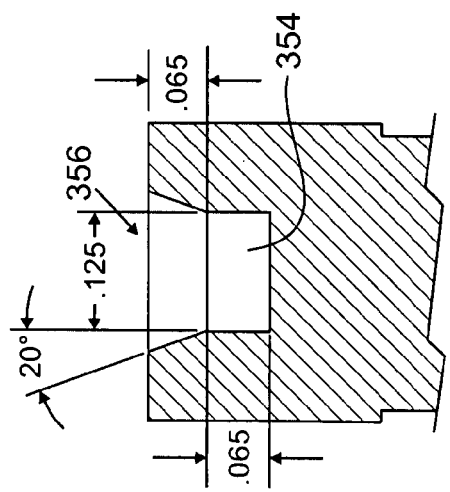

FIGS. 3A and 3B illustrate an example use of a protective corneal applanator device 102 according to one embodiment of this disclosure. Among other things, FIG. 3A illustrates a top view of the protective corneal applanator device 102 shown in FIG. 2, and FIG. 3B illustrates a fiber optic holder shaft 350 used to mount optical fibers on the protective corneal applanator device 102. Other embodiments of the protective corneal applanator device 102 may be used without departing from the scope of this disclosure. Also, for ease of explanation, the protective corneal applanator device 102 may be described as operating in the system 100 of FIG. 1. The protective corneal applanator device 102 could be used in any other suitable system.

As shown in FIG. 3A, the protective corneal applanator device 102 is attached to a vacuum syringe 302. The vacuum syringe 302 is used to evacuate the suction ring 214, which attaches the protective corneal applanator device 102 to the patient's eye 104. For example, a vacuum of approximately 100 to 700 mm Hg (with respect to a standard atmospheric pressure of 760 mm Hg) may be used to attach the protective corneal applanator device 102 to the patient's eye 104. Flexible plastic tubing 304 connects the vacuum port 220 of the protective corneal applanator device 102 to the vacuum syringe 302. The vacuum syringe 302 could represent any suitable structure capable of causing suction in the suction ring 214. The vacuum syringe 302 may, for example, be designed for ophthalmic applications, such as vacuum syringes used to provide suction to a microkeratome (a device used as part of a LASIK procedure). As a particular example, the vacuum syringe 302 could represent an Oasis Medical Model 0490-VS vacuum syringe.

A plunger 306 of the vacuum syringe 302 is normally held open by a spring 308 to separate the plunger top 310 from the syringe body top 312 at a suitable spacing, such as approximately 3 cm. A surgeon or other physician depresses the plunger 306 of the vacuum syringe 302 prior to placement of the suction ring 214 on the cornea 204 of the patient's eye 104. The surgeon or other physician may then place the protective corneal applanator device 102 onto the patient's cornea 204 until the cornea 204 is applanated out to, for example, approximately the 10 mm optical zone. Once the protective corneal applanator device 102 is in place, the surgeon or other physician releases the plunger 306 of the vacuum syringe 302 to produce a pressure differential that provides partial suction to hold the protective corneal applanator device 102 onto the patient's cornea 204.

As shown in FIG. 3B, a fiber optic holder shaft 350 could be used to mount a set of optical fibers on the protective corneal applanator device 102. For example, the shaft 350 could be used to accurately mount the optical fibers in a predetermined geometrical array with respect to the number, pattern, and spacing of the optical fibers.

The shaft 350 could be constructed from any suitable material(s), including a lightweight inert material (such as aluminum or plastic) that is machined to include a set of channels 352 in which the optical fibers are mounted. The shaft 350 could also include a small permanent magnet 354 (such as a 3 mm diameter, 1.5 mm thick NdFeB magnet) that is mounted in a depression 356 in the end of the shaft 350 that contacts the transparent window 210 of the protective corneal applanator device 102. The depression 356 may have the same depth as the thickness of a small permanent magnet (focusing and centration aid and mask 216) that is mounted on the transparent window 210. The two magnets are mounted so that they attract each other, and this attractive magnetic force facilitates the placement of an optical fiber array (mounted in the fiber optic holder shaft 350) on the surface of the transparent window 210 with accurate centration. Since the optical fibers are also mounted with their faces in the same plane as the edge of the fiber optic holder shaft 350, the optical fibers are thereby accurately placed so that light emerging from each optical fiber has the same irradiance distribution at the surface of the transparent window 210. In other embodiments, the optical fibers could be mounted at other uniform distances from the transparent window 210 in order to change the irradiance distribution.

In some embodiments, the fiber optic holder shaft 350 may have the dimensions shown in FIG. 3B. However, the dimensions shown in FIG. 3B are for illustration only. Other fiber optic holder shafts with other dimensions could also be used.

Although FIGS. 3A and 3B illustrate example uses of a protective corneal applanator device 102, various changes may be made to FIGS. 3A and 3B. For example, other mechanisms besides a vacuum syringe 302 could be used to produce suction at the suction ring 214 of the protective corneal applanator device 102. Also, other mechanisms could be used to mount an optical fiber array on the protective corneal applanator device 102.

Figure 4:
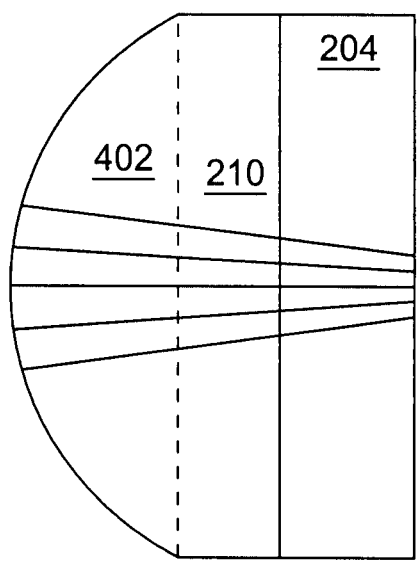
FIG. 4 illustrates an example microlens that could be mounted in a protective corneal applanator device according to one embodiment of this disclosure.

FIG. 4 illustrates an example microlens 402 that could be mounted in a protective corneal applanator device 102 according to one embodiment of this disclosure. In particular, FIG. 4 illustrates a portion of the transparent window 210 of the protective corneal applanator device 102 having a convex microlens 402 on its surface. The embodiment of the microlens 402 shown in FIG. 4 is for illustration only. Other embodiments of the microlens 402 may be used without departing from the scope of this disclosure. Also, for ease of explanation, the microlens 402 may be described in conjunction with the protective corneal applanator device 102. The microlens 402 could be used in any other suitable device.

In the protective corneal applanator device 102, refractive or diffractive micro-optics can be used to change the spatial distribution of laser irradiation. In other words, the transparent window 210 may have microlenses 402 on its anterior surface to alter how light energy 218 is directed onto the cornea 204 of the patient's eye 104. In this example, in the refractive case, a convex microlens 402 at the front surface of the transparent window 210 can be used to focus a collimated laser beam. The microlens 402 helps to provide constant laser irradiance (after absorption loss) at each depth within the cornea 204. As a particular example, the microlens 402 could help to provide constant laser irradiance at each depth within the cornea 204 for an absorption coefficient of 20 cm$^{-1}$ (the approximate temperature-averaged value for a pulsed Ho:YAG laser wavelength).

In FIG. 4, light rays are focused into the cornea 204 by the convex microlens 402. As a particular example, the convex microlens 402 could have a radius-of-curvature of 1.12 mm, and an initial spot radius of 0.3 mm could be reduced to 0.19 mm at the window/cornea interface and to 0.12 mm at the posterior surface of the cornea 204. Also shown in FIG. 4 is the refraction required to focus light rays from, for example, a 0.38 mm diameter spot size at the anterior corneal surface to, for example, a 0.24 mm diameter spot size at the posterior corneal surface. With this amount of focusing, the irradiance may be constant throughout the corneal thickness for an absorption coefficient of 20 cm$^{-1}$. Constant irradiance may produce a constant temperature rise as a function of depth, so the protective corneal applanator device 102 may more efficiently cool the corneal epithelium. The microlens 402 on the transparent window 210 could be even more convex (with a smaller radius-of-curvature) to produce even more focusing if desired.

An array of these microlenses 402 could be fabricated on the front surface of the transparent window 210 to provide focusing for an array of laser beams, such as a 16-spot pattern of 8 spots per ring at ring centerline diameters of 6 mm and 7 mm (as is one standard pattern presently used for LTK treatments). For example, several of these microlenses 402 could be mounted in the protective corneal applanator device 102 in order to match the array of optical fibers that deliver light to the cornea 204. As a particular example, if sixteen fibers are used in the array, sixteen microlenses could be mounted in alignment with each of the sixteen fibers. The microlenses 402 then focus the output light of each optical fiber within the cornea 204.

Although FIG. 4 illustrates one example of a microlens 402 that could be mounted in a protective corneal applanator device 102, various changes may be made to FIG. 4. For example, the protective corneal applanator device 102 need not include any microlenses 402 on the transparent window 210. Also, diffractive optics (such as those involving an optical coating on the front surface of the transparent window 210 that diffracts incident light energy 218) could also be used to obtain a desired spatial distribution of the light energy 218 as a function of corneal depth.

FIGS. 5 through 8 illustrate example temperature distributions within corneal tissue during a cornea reshaping procedure according to one embodiment of this disclosure. For ease of explanation, FIGS. 5 through 8 are described with respect to a cornea reshaping procedure involving the protective corneal applanator device 102 operating in the system 100 of FIG. 1. However, the protective corneal applanator device 102 and the system 100 could operate a manner different from that shown in FIGS. 5 through 8.

Figure 5:
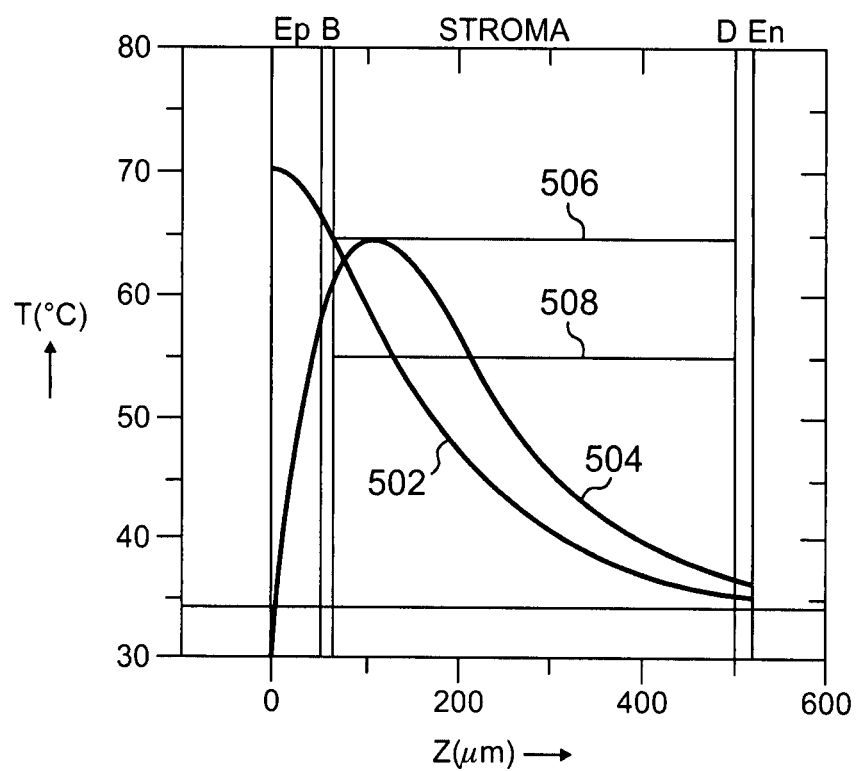
FIGS. 5 through 8 illustrate example temperature distributions within corneal tissue during a cornea reshaping procedure according to one embodiment of this disclosure.

FIG. 5 illustrates the results of one-dimensional thermal modeling calculations of temperature distributions as a function of depth of penetration Z into corneal tissue according to one embodiment of this disclosure. In particular, FIG. 5 is a graphic representation of the temperature in the various layers of the cornea 204 produced by heating the cornea 204 using light energy 218 from a continuous wave hydrogen fluoride laser. FIG. 5 also shows the effectiveness of using a heat sink that is provided by the protective corneal applanator device 102.

In FIG. 5, typical depths of microstructural layers of the cornea 204 are indicated for the epithelium (Ep), Bowman's layer (B), the stroma, Descemet's membrane (D), and the endothelium (En). The calculations use estimated thermal properties (thermal conductivity, thermal diffusity, and heat capacity) for human corneas, together with the optical absorption coefficients for laser wavelengths produced by a continuous wave hydrogen fluoride chemical laser.

The line 502 in FIG. 5 represents the temperature distribution in the cornea 204 without the use of the protective corneal applanator device 102. The line 504 in FIG. 5 represents the temperature distribution in the cornea 204 when the protective corneal applanator device 102 is used. The temperature distribution represented by line 502 peaks on the anterior surface (Z=0) of the cornea 204. It represents the application of a continuous wave hydrogen fluoride chemical laser source at a predetermined wavelength $\lambda$ of approximately 2.61 μm at a fixed irradiance of 30 W/cm$^2$ and a fixed time of 80 ms. The temperature distribution represented by line 504 peaks within the anterior portion of the stroma. It represents the application of a continuous wave hydrogen fluoride chemical laser source at the same laser wavelength at a fixed irradiance of 100 W/cm$^2$ and a fixed time of 100 ms. The desired temperature range (approximately 55° C. to 65° C.) for stromal modification without thermal damage (even to keratocytes) is shown within the corneal stroma by lines 506-508.

As shown in FIG. 5, the use of the protective corneal applanator device 102 helps to keep the temperature of the corneal epithelium below temperatures at which damage to the corneal epithelium would occur, even when a laser with higher irradiance is used for a longer time period. With the temperature cooling provided by the device 102, light energy 218 of a higher irradiance level with a longer exposure time may result in harmless temperatures in the epithelium and Bowman's layer of the cornea 204 while allowing functionally effective temperatures for photothermal keratoplasty or other treatment within the anterior part of the stroma.

Figure 6:
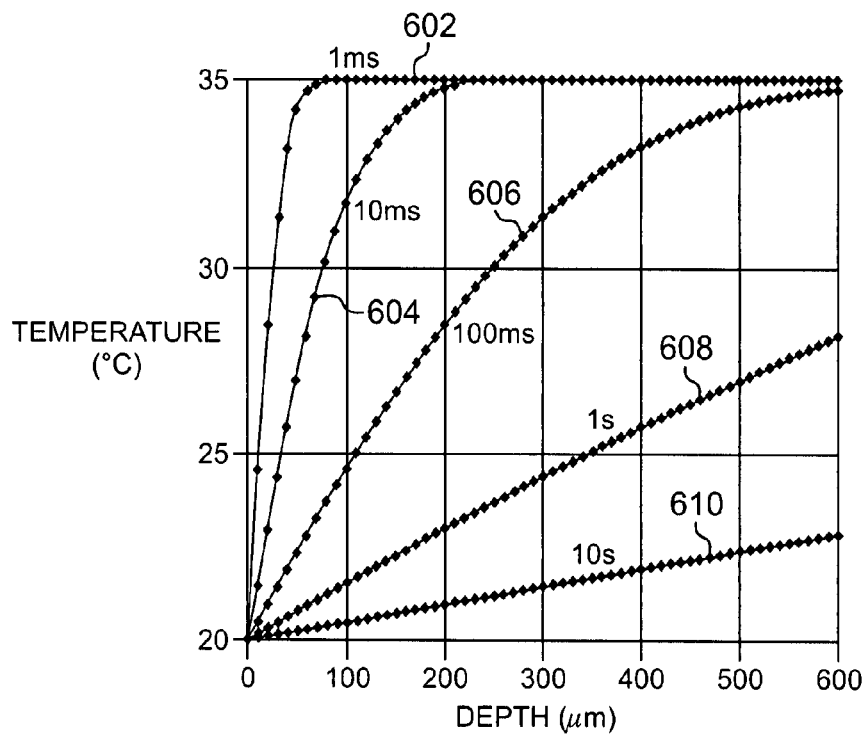

FIG. 6 illustrates temperature distributions as a function of depth of penetration Z into corneal tissue at various times after contact of the cornea 204 with the protective corneal applanator device 102 prior to treatment. In particular, passive cooling may be performed prior to irradiation of the cornea 204. The individual data symbols in FIG. 6 on each distribution are at 10 μm intervals. Also, the temperature distributions occur after contact of the transparent window 210 (made of sapphire at 20° C.) with the cornea 204 (at 35° C. before contact, although actual corneal temperatures may vary, such as in a range of approximately 33° C. to approximately 36° C.).

As represented by the line 602, for a 1 ms contact time, there is a temperature difference of approximately 13° C. from the front surface (z=0) through the depth of the corneal epithelium to the epithelial basement membrane/Bowman's layer interface (at approximately z=50 μm). As represented by the line 604, for a 10 ms contact time, the difference has decreased to approximately 6° C. As represented by the line 606, for a 100 ms contact time, the difference has decreased to approximately 2-3° C. As represented by the lines 608-610, for contact times of 1 s and 10 s, respectively, the difference is less than 1° C.

Based on this, on the timescale of mounting the protective corneal applanator device 102 on a patient's eye 104 and preparing the system 100 for treatment, heat flow is essentially completed and a "steady-state" temperature at approximately room temperature has been established in the anterior of the cornea 204. As shown in FIG. 6, a small temperature difference from the anterior surface (z=0) to the posterior surface (approximately z=600 μm) of the cornea 204 still remains.

In some embodiments, the rapid temporal evolution of the anterior cornea temperature to that of the transparent window 210 allows the device 102 to function as a thermostat. Over a timescale of tens of seconds to hundreds of seconds, the anterior cornea temperature may be regulated at or near $T_0$. However, the device 102 may not represent an infinite heat sink. As a result, at much longer timescales, the device 102 may tend to heat up, possibly to some temperature above $T_0$ at which heat flow from the cornea 204 into the device 102 is balanced by heat losses from the device 102 (such as by convection and radiation). A larger temperature difference between the anterior surface (z=0) and the epithelial basement membrane/Bowman's layer interface in the patient's eye 104 can be achieved by cooling the transparent window 210 in the device 102 to an initial temperature $T_0$ below room temperature. This may involve active or dynamic cooling as described above.

Dynamic cooling of the transparent window 210 could also yield temperature distributions similar to those represented by lines 602-604 in FIG. 6, but with a larger temperature range from approximately 0° C. at z=0 μm to 35° C. at large z (approximately 100 to 200 μm). The dynamic cooling procedure may work well for pulsed Ho:YAG or other laser irradiation if a sequence of pulses for releasing a cryogen or other liquid is synchronized with the sequence of laser pulses to provide pre-cooling of the window 210 at the same time before each laser pulse. The procedure may also be useful for continuous wave laser irradiation if a cooling pulse is "stretched" to provide continuous cooling for a timescale comparable to the length of the continuous wave laser irradiation.

Figure 7:
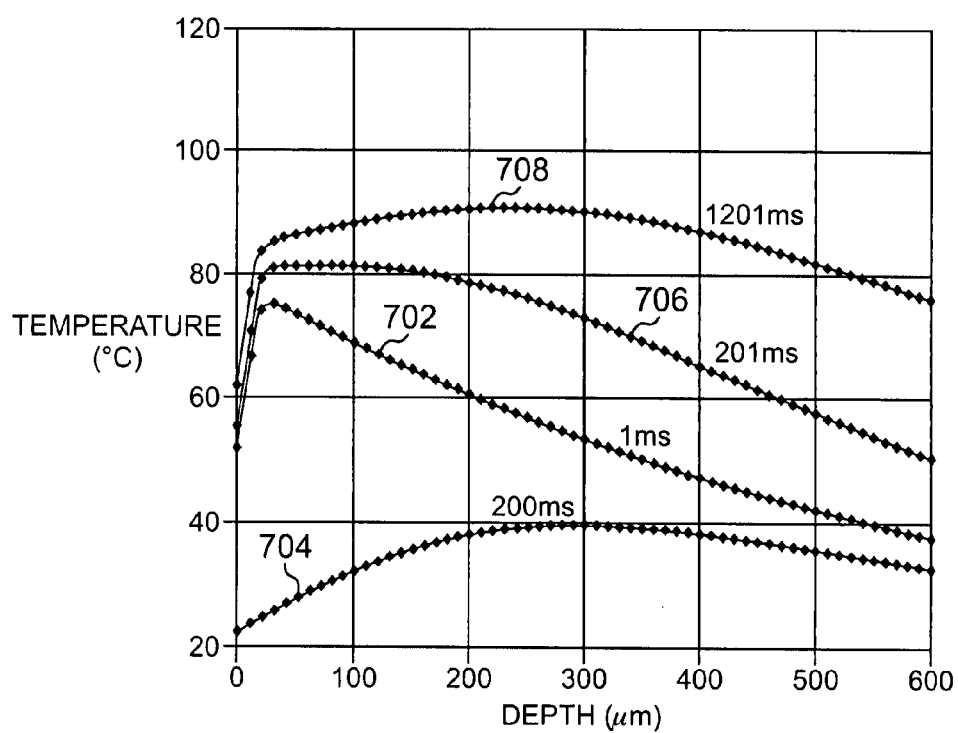

FIG. 7 illustrates temperature distributions as a function of depth of penetration Z into corneal tissue at various times during treatment with a pulsed laser 106. Just prior to irradiation, the cornea 204 may be cooled to near room temperature and may have a small temperature gradient, with temperature increasing as a function of depth from the transparent window/cornea interface (z=0). If a pulsed laser 106 is used (such as a Ho:YAG laser), the first laser pulse irradiates the cornea 204, and an almost instantaneous temperature rise may occur during the pulse duration (such as 200s). There may be some heat transfer from the cornea 204 into the transparent window 210 during this pulse (and during subsequent pulses, such as the 7-pulse sequence that is used in current LTK treatments). In the period (such as 200 ms) between successive pulses, the transparent window 210 removes additional heat from the cornea 204, and heat also flows from the anterior portion of the cornea 204 into the posterior (cooler) portion of the cornea 204 between laser pulses.

This transfer of heat is illustrated in FIG. 7. In particular, FIG. 7 illustrates the temperature distributions (in the irradiated spot center) at several times after pulsed Ho:YAG laser irradiation of a cornea 204 in contact with an Infrasil quartz window 210 at 20° C. Individual data symbols on each distribution are at 10 μm intervals.

In this example, the first laser pulse starts at t=0 and finishes at t=0.2 ms, the second pulse starts at t=200 ms and finishes at t=200.2 ms, and so on. The calculations shown are for a cornea 204 (in contact with a 0.6 mm thick Infrasil quartz window 210 applanating its anterior surface 206) with temperature-averaged thermal properties and an absorption coefficient of approximately 20 cm$^{-1}$, which is irradiated by a pulsed Ho:YAG laser using a radiant exposure of 10.7 J/cm$^2$ with a flat-top beam of 600 μm diameter. These parameters are similar to those used for the "standard" treatment of 242 mJ/pulse.

Only temperature distributions due to laser pulses 1, 2 and 7 (of a 7-pulse train) are shown in FIG. 7. The first laser pulse produces the temperature distribution represented by line 702, which has a peak temperature of approximately 75° C. at a depth z=approximately 32 μm. This is presumably in the epithelium (which has been measured to be 51±4 μm thick in n=9 eyes by in vivo confocal microscopy and 59.9±5.9 μm thick in n=28 eyes by optical coherence tomography). Cooling between pulses 1 and 2 leads to the residual temperature distribution represented by line 704, with a peak temperature of approximately 40° C. at a depth z=approximately 300 μm. The second laser pulse produces the temperature distribution represented by line 706 and has a peak temperature of approximately 81° C. at a depth z=approximately 64 μm. This trend toward higher peak temperatures, with movement of the peak to greater depths, continues over the full 7-pulse train. The seventh laser pulse produces the temperature distribution represented by line 708, with a peak temperature of approximately 91° C. at a depth z=approximately 230 μm. A sapphire window 210 may be a more efficient heat sink than an Infrasil quartz window 210. As a result, anterior corneal temperatures would be lower than those shown in FIG. 7.

Figure 8:
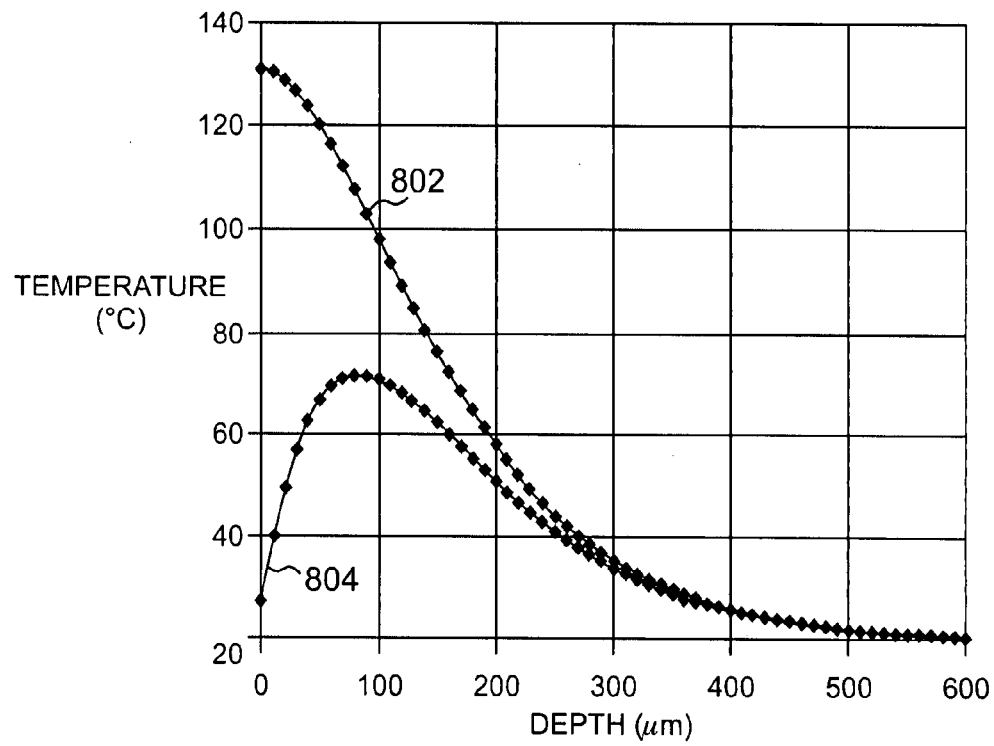

FIG. 8 illustrates temperature distributions as a function of depth of penetration Z into corneal tissue at various times after irradiation during treatment with a continuous wave laser. In particular, FIG. 8 illustrates temperature distributions from thermal modeling calculations in the irradiated spot center at 103 ms after continuous wave laser irradiation. The calculations shown are for a bare cornea 204 (represented by line 802) and for a cornea 204 in contact with a 1.5 mm thick sapphire window 210 at 20° C. applanating its anterior surface 206 (represented by line 804). Individual data symbols on each distribution are at 10 μm intervals.

Both cases in FIG. 8 use temperature-averaged cornea thermal properties, and both cases involve continuous wave laser irradiation using an irradiance of 70 W/cm$^2$ with a flat-top beam of 1 mm diameter. The absorption coefficient is 100 cm$^{-1}$ (in contrast to the temperature-averaged value for the pulsed Ho:YAG laser used in FIG. 7, which was approximately 20 cm$^{-1}$). The larger absorption coefficient is appropriate for a continuous wave thulium fiber laser operating at approximately 1.93 μm wavelength.

With the sapphire window 210 acting as a heat sink, the cornea temperature distribution represented by line 804 has a peak temperature of approximately 72° C. at a depth z=approximately 80 μm. The basal epithelium is much cooler (approximately 66° C. at z=50 μm) compared to the pulsed laser irradiation case shown in FIG. 7, and the entire epithelium is well below the thermal damage threshold temperature (estimated to be approximately 70-75° C. for 1 s irradiation). This level of epithelial protection may be sufficient to prevent damage to the epithelial basement membrane, which may be needed to prevent a fibrotic wound healing response leading to regression of refractive correction. This efficient passive heat sink effect may occur even though the absorption coefficient for the continuous wave laser is 100 cm$^{-1}$, rather than 20 cm$^{-1}$ for the pulsed Ho:YAG laser.

In the continuous wave laser case shown in FIG. 8, the cornea 204 is smoothly heated to its peak temperature during a single laser irradiation of approximately 100 ms duration. In the pulsed laser case of FIG. 7, the cornea is subjected to rapid heating after each laser pulse, followed by cooling periods, during a sequence of seven pulses at 5 Hz pulse repetition frequency.

Further protection of the corneal epithelium can be achieved by changing the temporal or spatial distribution of laser irradiation. For example, in the continuous wave laser case, if the laser irradiance is decreased so that the same total energy is delivered over a longer irradiation time, the peak of the temperature distribution may move to greater depth, and the temperature of the basal epithelium may be decreased further. The laser irradiance can also be increased over the total irradiation time so that the initial temperature distribution is peaked more posteriorly in the cornea 204 due to decreased irradiance, followed by further heating at higher irradiance to build on the initial temperature distribution. In addition to using passive heat sink cooling during irradiation, active cooling, dynamic cooling, micro-optics, and micro-optic arrays could be used as described above. Combinations of temporal and spatial shaping of the incident laser beam can also be used to produce a desired temperature distribution within an irradiated cornea 204.

Although FIGS. 5 through 8 illustrate examples of temperature distributions within corneal tissue during a cornea reshaping procedure, various changes may be made to FIGS. 5 through 8. For example, FIGS. 5 through 8 often illustrate results observed or modeled for particular treatments using particular types of lasers 106 and particular types of light energy 218. Other lasers or light energy could be used during treatment. Also, FIGS. 5 through 8 are only provided as an illustration of various possible embodiments of the system 100 and do not limit this disclosure to particular embodiments.

Figure 9A:
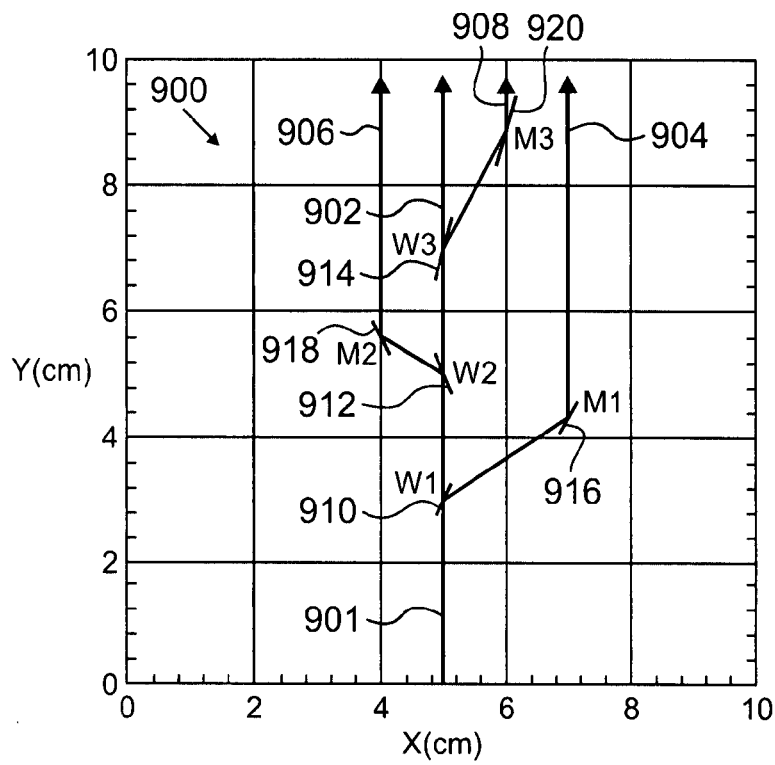
FIGS. 9A through 9D illustrate example beam splitting systems according to one embodiment of this disclosure.
Figure 9B:
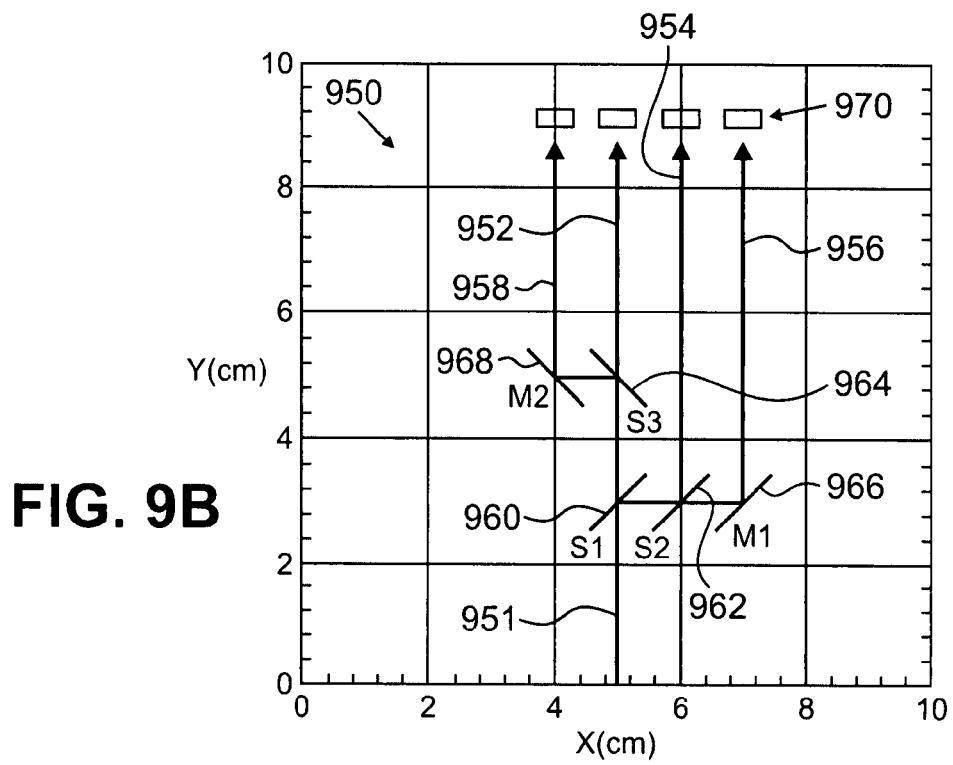
Figure 9D:
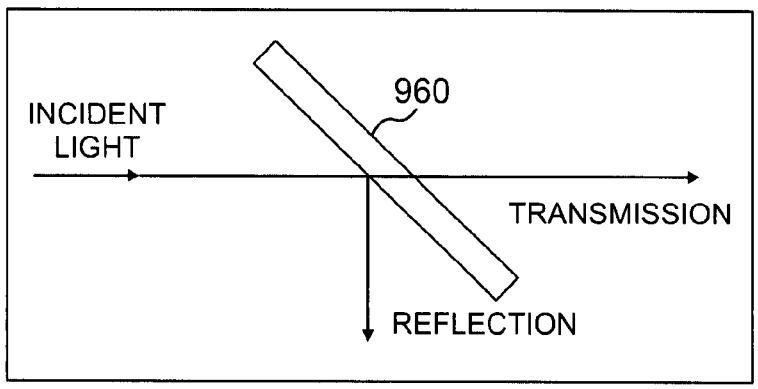
Figure 9C:
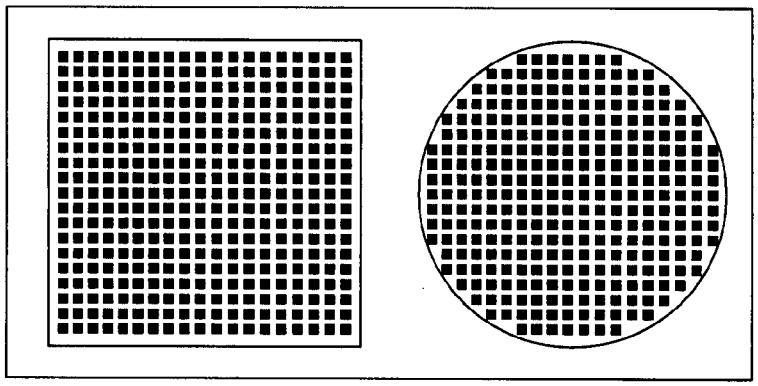

FIGS. 9A through 9D illustrate example beam splitting systems according to one embodiment of this disclosure. In particular, FIGS. 9A and 9B illustrate beam splitting systems 900 and 950, and FIGS. 9C and 9D illustrate an example component used in the beam splitting system 950 of FIG. 9B. For ease of explanation, the beam splitting systems shown in FIGS. 9A through 9D are described with respect to the system 100 of FIG. 1. The beam splitting systems shown in FIGS. 9A through 9D could be used in any other suitable system, whether or not that system is used to correct ocular refractive errors.

The beam splitting systems shown in FIGS. 9A and 9B generate multiple beams for output. Using multiple beams during an LTK or other procedure may provide various benefits over using a single beam. For example, some astigmatism could be induced in the patient's eye 104 by asymmetric irradiations. The use of multiple beams in a symmetric pattern may provide more symmetric irradiations and enable simultaneous treatment of multiple spots on the cornea 204.

As shown in FIG. 9A, a beam splitting system 900 splits a main laser beam 901 into multiple beams 902-908 (called "beamlets"). The main laser beam 901 passes through three windows 910-914. Each of the windows 910-914 reflects a portion of the main laser beam 901 to produce the beamlets 904-908. Mirrors 916-920 redirect the beamlets 904-908 to propagate parallel to the original laser beam 901, which remains as beamlet 902.

Each of the mirrors 916-920 represents any suitable structure for redirecting a beamlet. Each of the windows 910-914 represents any suitable structure for partially reflecting a laser beam to create an additional beamlet. For example, the windows 910-914 could represent sapphire windows. In some embodiments, the windows 910-914 are oriented at different angles of incidence so that their reflections (from both air/window surfaces) exactly distribute the four beamlets 902-908 with the same energy (25% of the original laser beam energy). This can be accomplished because the reflectance is a function of the angle of incidence (measured from a normal to the window surface). For sapphire windows 910-914, the index of refraction (ordinary ray) is approximately 1.739 at a 1.93 μm wavelength (the operating wavelength for a continuous wave thulium fiber laser), leading to required angles of incidence θ=approximately 63.4°, 63.6° and 76.6° for windows 910-914, respectively, for an initially unpolarized laser beam.

Although a continuous wave thulium fiber laser beam is initially unpolarized (which can be represented as a superposition of equal amounts of s-polarized and p-polarized component beams), reflectances differ for s-plane (perpendicular to the plane defined by the incident beam and the reflected beam) and p-plane (parallel to the plane) polarizations. As a result, the unreflected beam transmitted through the window 910 may become polarized. To compensate for this polarization (and to compensate for the loss in intensity of the s-polarized component of the beam), the window 912 may be rotated 900 so that its reflection is out of the XY plane. Then, s-plane and p-plane orientations are switched, reflectances are switched, and the unreflected beam transmitted through the window 912 is unpolarized once again. A final reflection at the window 914 produces the third reflected beamlet. Additional mirrors may then be used to direct the beamlets 904, 908 into a vertical array lined up with the beamlet 902 and the out-of-plane beamlet 906. The final result is a linear vertical array in the Z-direction.

In other embodiments, the windows 910-914 may be replaced with sets of sapphire and/or calcium fluoride ($CaF_2$) windows that are stacked in subsets to reflect beamlets of near-equal energy. For example, the window 910 may be replaced with a stack of one sapphire window and two $CaF_2$ windows (which provide 24.08% of the energy in a first reflected beamlet 904). The window 912 may be replaced with two sapphire windows and one $CaF_2$ window (which provide 23.19% of the energy in a second reflected beamlet 906). The window 914 may be replaced with four sapphire windows (which provide 23.92% of the energy in a third reflected beamlet 908). The remaining transmitted laser beam represents beamlet 902 and provides 28.81% of the remaining energy. The exact energies (all of which are given for near-normal angles of incidence) of the four beamlets 902-908 can then be balanced with attenuators.

FIG. 9B illustrates another example beam splitting system 950. As shown in FIG. 9B, a main laser beam 951 is split into four beamlets 952-958 by 50/50 perforated beam splitters 960-964. Two turning mirrors 966-968 redirect two of the reflected beamlets 956-958, and the beam splitter 962 reflects the beamlet 954. The original laser beam 951 propagates to form the beamlet 952. Focusing lenses 970 may be mounted at the four beamlet positions to focus the beamlets into, for example, the fiber optic array 110. In particular embodiments, each of the beam splitters 960-964 in FIG. 9B has a 12.7 mm diameter and is oriented at 45°, each of the turning mirrors 966-968 has a 12.7 mm diameter, and the focusing lenses 970 are mounted at a position of Y=approximately 9 cm.

In some embodiments, the perforated beam splitters 960-964 include a pattern of reflecting areas (such as dots or squares) that cover a specified percentage of a window as shown in FIG. 9C. In this case, a 50/50 beam splitter (such as splitter 960) reflects 50% and transmits 50% of a beam as shown in FIG. 9D. In particular embodiments, the reflecting areas are 106 μm by 106 μm aluminum film squares (with a protective overcoating) spaced at 150 μm center-to-center in X and Y intervals. Also, the window material could represent BK7 glass, which has nearly 100% internal transmission (for a path length of 1.5 mm) at approximately 2 μm, which is the operating wavelength of the continuous wave thulium fiber laser. In addition, at least one window/air surface may have an anti-reflection coating. The reflective areas may be deposited by a photolithography process or formed in any other suitable manner.

Other beam splitter optics could be used to generate a four-beam array, such as a set of multilayer dielectric coated windows that have specified reflectances at specified angles-of-incidence. Also, other techniques could be used to generate a multiple beam array in the system 100 of FIG. 1, such as using a 1×4 fiber optic splitter in which one optical fiber is split into four optical fibers.

Although FIGS. 9A through 9D illustrate examples of beam splitting systems, various changes may be made to FIGS. 9A through 9D. For example, while FIGS. 9A and 9B illustrate the generation of four beamlets, similar techniques could be used to generate other numbers of beamlets with approximately equal energy, such as eight beamlets, sixteen beamlets, or some other number of beamlets that produce an axisymmetric irradiance distribution on the cornea 204. As a particular example, the structure shown in FIGS. 9A or 9B could be replicated to process each of the beamlets output in FIGS. 9A or 9B, where each replicated structure would receive and split a beamlet. The axisymmetric irradiance distribution may involve two or more sets of beamlets directed onto the cornea 204 in rings of spots (such as those shown in FIG. 11B, which is described below). Each of the rings may be delivered with the same laser energy/spot, or the rings may be delivered with different energies/spot in each ring in order to produce desired changes in one or more radii of curvature of the cornea 204. For instance, it may be desirable to perform cornea reshaping into a more prolate aspherical shape than the normal cornea. A more prolate aspherical shape may have annular zones of refraction that provide both fine distance and fine near visual acuity for patients with presbyopia. In other embodiments, the beamlets of laser light could be adjusted so that they have unequal energies in order to produce a non-axisymmetric irradiance distribution. This non-axisymmetric irradiance distribution could be adjusted to correct non-axisymmetric refractive errors, such as some types of irregular astigmatism.

Figure 10:
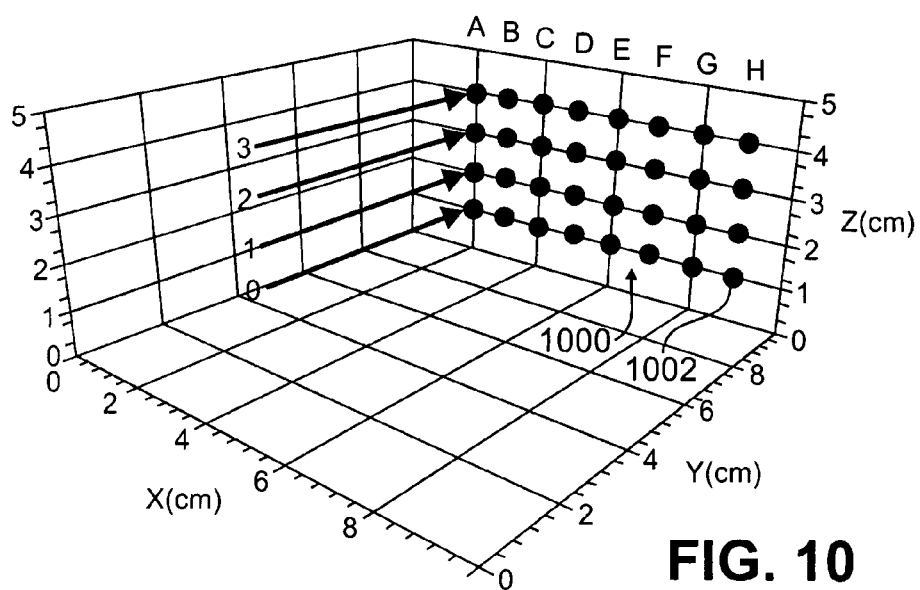
FIG. 10 illustrates an example linear four-beam array matching a fiber optic array in a beam distribution system according to one embodiment of this disclosure.

FIG. 10 illustrates an example linear four-beam array 1000 matching a fiber optic array in a beam distribution system according to one embodiment of this disclosure. In particular, FIG. 10 illustrates a linear four-beam array 1000 that provides the four beamlets produced by the beam splitting systems of FIGS. 9A through 9D to the fiber optic array 110 of FIG. 1. The linear four-beam array 1000 could be used with any other suitable beam splitting system or in any other suitable system.

As shown in FIG. 10, a 4×8 array 1000 of optical fiber inputs 1002 is shown. The first four-fiber array (labeled "A") directs four beamlets onto the cornea 204 of the patient's eye 104 at a set of predetermined positions. After these spots are irradiated, the translation stage 112 moves the fiber optic array 110 so that the second four-fiber array (labeled "B") directs the beamlets onto the patient's cornea 204 at another set of predetermined positions. Similarly, if required for a particular LTK or other procedure, the arrays labeled "C" through "H" may be used to direct the beamlets onto the patient's cornea 204 for a total of up to 32 different irradiated spots. In some embodiments, fewer than 32 irradiated spots are needed, such as when an LTK or other procedure irradiates 16 or 24 different locations on the cornea 204. In this case, fewer four-fiber arrays are needed in the array 1000. Also, additional four-fiber arrays may be used to provide for the irradiation of additional locations on the cornea 204.

Although FIG. 10 illustrates one example of a linear four-beam array 1000 matching a fiber optic array in a beam distribution system 108, various changes may be made to FIG. 10. For example, the array 1000 could include more or less groups of four-fiber arrays. Also, each fiber array could include more or less fibers (and is not limited to groups of four). In addition, this mechanism could be replaced in the system 100 of FIG. 1 with, for example, a 1×4 fiber optic splitter.

Figure 11A:
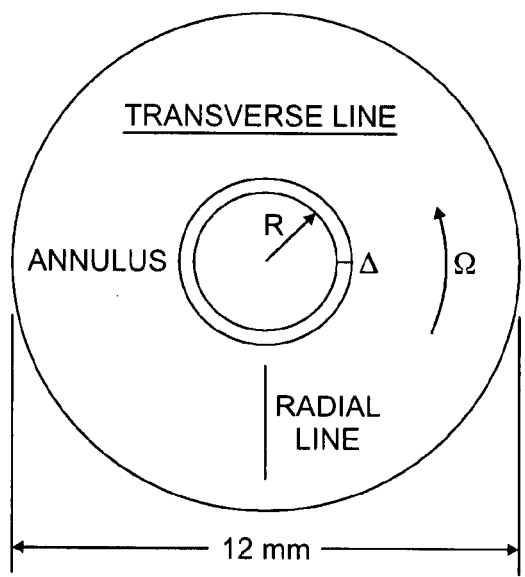
FIGS. 11A through 11C illustrate example patterns of treatment during a cornea reshaping procedure according to one embodiment of this disclosure.
Figure 11B:
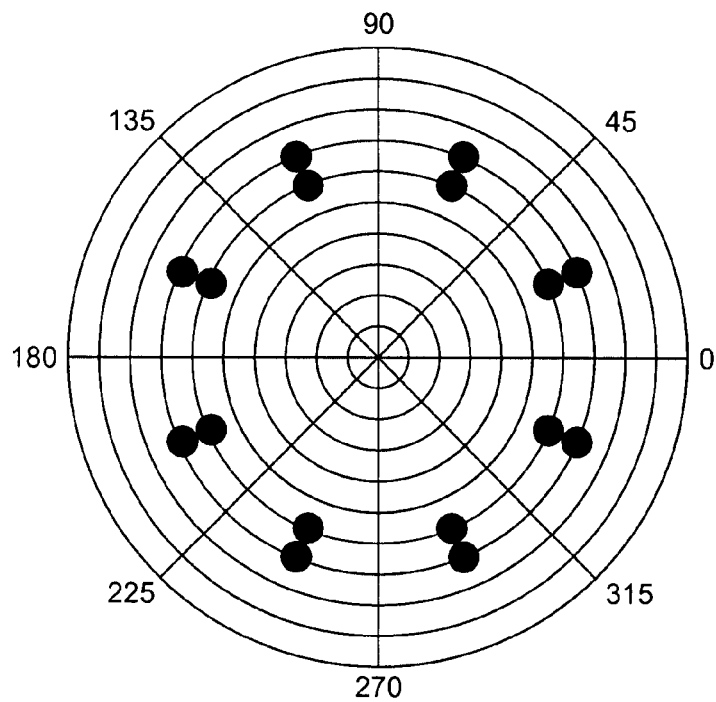
Figure 11C:
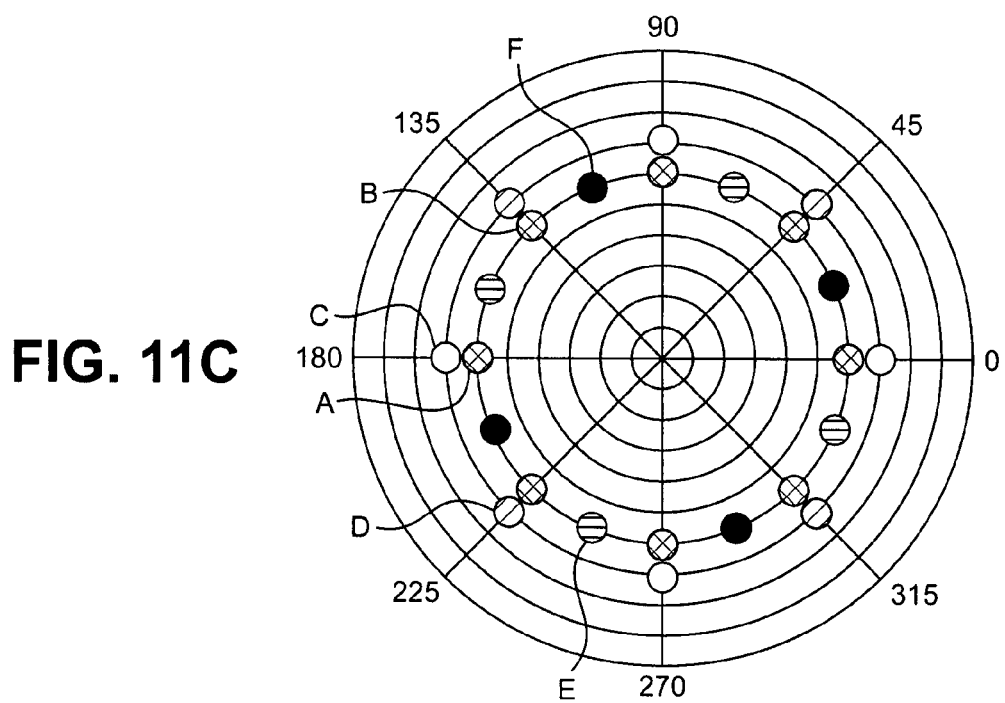

FIGS. 11A through 11C illustrate example patterns of treatment during a cornea reshaping procedure according to one embodiment of this disclosure. For ease of explanation, the patterns of treatment shown in FIGS. 11A through 11C are described with respect to the system 100 of FIG. 1. The patterns of treatment could be used by any other suitable system.

FIGS 11A through 11C are schematic representations of different patterns of treatment on the anterior surface 206 of the cornea 204. In FIG. 11A, a treatment annulus pattern has a radius R and a width Δ and is drawn using a laser spot that is slewed at an angular velocity Ω. FIG. 11A also shows radial and transverse treatment lines that may be drawn on the cornea 204. In FIG. 11B, two symmetrical concentric rings (each with eight spots) are irradiated onto the cornea 204. In FIG. 11C, two symmetrical concentric rings (one with eight spots and another with sixteen spots) are irradiated onto the cornea 204. In particular embodiments, each spot in FIGS. 11B and 11C may be approximately 0.6 mm in diameter, and the rings may be located at 6 mm and 7 mm centerline diameters (with the spots on radials extending from the corneal center). FIG. 11C labels various dot patterns with the labels "A" through "F", which correspond to the four-fiber arrays shown in FIG. 10.

Various geometric patterns and temporal periods of radiation may produce corrections of different types and magnitudes of ocular refractive errors. FIGS. 11A through 11C illustrate various geometric patterns and spatial orientations of treatment zones that provide a desired corrective effect. These patterns may be provided on one or more surfaces of the focusing and centration aid and mask 216 using an array of optical fibers. These patterns may also be provided by scanning a continuous wave laser beam over the surface of the cornea 204.

As shown in FIG. 11A, tangential lines, radial lines, annular rings, and combinations may be useful in obtaining corrective measures. As shown in FIGS. 11B and 11C, for one embodiment useful for the correction of hyperopia, light energy is applied as a geometric predetermined pattern of spots. In these examples, the various treatments result in patterns of shrinkage. In particular embodiments, the central optical zone 208 of the cornea 204 is not impacted, and all light energy applications are to the paracentral and peripheral regions (outside the 3 mm to 4 mm diameter central optical zone 208) of the cornea 204. Such an application regimen may substantially limit risk to patients since the critical central optical zone 208 is not actually treated.

In particular embodiments, at no time during or after application of the functionally effective dose of light energy 218 should there be a substantial corneal wound healing response, specifically fibrotic wound healing in the stromal tissue of the cornea 204. A substantial corneal wound healing response may be avoided by careful control of the nature and extent of stromal alteration and by the protection of the corneal epithelium (and the epithelial basement membrane) from thermal damage. Therefore, the results of the corneal reshaping produced by application of a functionally effective dose of light are predictable and controllable and are not subject to long-term modification due to a substantial corneal wound healing response. The functions of the protective corneal applanator device 102 include acting as any combination of: (1) a transparent window to permit light irradiation of the cornea 204; (2) a corneal applanator; (3) a heat sink to protect the corneal epithelium from thermal damage; (4) a thermostat to control the initial temperature of the anterior surface 206 of the cornea 204; (5) a geometrical reference plane for the cornea 204; (6) a positioner and restrainer for the eye 104; (7) a mask during the cornea reshaping procedure; (8) a focusing and centration aid for light irradiation in a predetermined pattern; and (9) a corneal hydration controller.

As noted above, the heat sink cooling process may be passive with no active or dynamic cooling performed. Sapphire or other material(s) may be used for this heat sink application in the transparent window. The table below illustrates the thermal properties of sapphire and other heat sink materials, as well as the cornea 204 itself.

| Property | Cornea | Infrasil | CaF$_2$ | Sapphire | Diamond |
|---|---|---|---|---|---|
| C$_P$ - heat capacity [units: J/g °C.] | 3.14 | 0.75 | 0.85 | 0.76 | 0.51 |
| K - thermal conductivity [units: W/cm °C.] | 0.00275 | 0.0126 | 0.097 | 0.218 | 20 |
| ρ - density [units: g/cm$^3$] | 1.11 | 2.20 | 3.18 | 3.98 | 3.52 |
| κ - thermal diffusivity [units: cm$^2$/s] | 0.00079 | 0.0076 | 0.036 | 0.072 | 11.1 |
| FOM—Figure-of-Merit (Eqn. 2) | 0.01 | 0.14 | 0.51 | 0.81 | 6.0 |

The data in this table pertain to a temperature of 20° C.

The thermal conductivity K is related to other properties by the following equation:

$$K = \rho C_p \kappa. \tag{1}$$

A "figure-of-merit" (FOM) for heat sink materials may be calculated using the following equation:

$$FOM = (K \rho C_p)^{1/2}. \tag{2}$$

FOM values are also listed in the table above. As shown in the table, diamond may be the best heat sink material among the listed window materials, but sapphire may have the second largest FOM value and may be less expensive.

During irradiation of the cornea 204 (as well as between laser irradiation pulses), thermal diffusion occurs through a thermal diffusion length or "thermal depth" (denoted $\delta_t$), which may have units of centimeters, micrometers, or other appropriate units. The thermal depth may be time-dependent and determined using the following formula:

$$\delta_t = 2(\kappa t)^{1/2}. \tag{3}$$

On the timescale between laser pulses (such as 0.2 s), the thermal depth could be approximately 80 μm for the cornea 204 and approximately 760 μm for sapphire. Hence, heat that flows from the cornea 204 into sapphire may be efficiently transported away from the cornea/sapphire interface. Since thermal diffusion is more rapid in sapphire compared to the cornea 204, heat transfer is "rate-limited" by thermal diffusion through the cornea 204.

When a sapphire window 210 (at room temperature $T_0$=approximately 20° C.) contacts the cornea 204 (at physiological temperature $T_p$=approximately 35° C., although this varies as a function of age, room temperature, and so on), heat flows from the warmer cornea 204 into the cooler heat sink. This heat transfer case is similar to the case of a semi-infinite solid (the cornea 204 and the rest of the body behind it) bounded at its anterior surface (z=0, the tear film/anterior epithelium) by a heat sink kept at a fixed temperature $T_0$. The analytical solution of this may be given as:

$$T(z,t)=T_0+\Delta T erf\{z/[2(\kappa t)^{1/2}]\} \quad (4)$$

where $\Delta T$ is the temperature difference ($T_p-T_0$) between the cornea 204 and the heat sink, and erf(x) is the error function. Combining Equations (3) and (4) leads to:

$$T(z,t)=T_0+66\ Terf\ [z/\delta_t]. \quad (5)$$

FIG. 6 shows T(z,t) calculations from Equation (5) for a sapphire heat sink contacted with the cornea 204.

A four-beam array may be optimal in some embodiments from the standpoint of using a relatively low power (such as 3W) continuous wave thulium fiber laser to irradiate fairly large spots (such as up to 1 mm diameter) on the cornea 204 in each laser energy delivery. For example, using a continuous wave thulium fiber laser operating at approximately 1.93 μm (for which the cornea absorption coefficient is approximately 100 cm$^{-1}$), the laser 106 may be capable of irradiating a set of spots at an irradiance in the range of 50 to 100 W/cm$^2$ in order to produce desired keratometric changes in periods of 100 ms to 200 ms duration. For an irradiance requirement of 100 W/cm$^2$, a 3W laser 106 can irradiate approximately 0.03 cm$^2$ of area simultaneously, which is equivalent to four spots of approximately 970 μm diameter/spot. A 6W laser 106 can irradiate eight spots of approximately 1 mm diameter simultaneously (assuming loss-free delivery of laser energy to each spot). If an allowance is made for a 33% loss, for example, the required laser power may be raised 50% to approximately 4.5W and approximately 9W for the four spot and eight spot cases, respectively. Of course, irradiation of smaller diameter (less than 1 mm) spots at the required irradiance can be accomplished with a lower power laser. A planning equation could be specified as:

$$P=3*(100/\alpha)*(n/4)*(\phi/1000)^2/(1-L), \quad (6)$$

or, combining factors, as:

$$P=(75n/\alpha)(\phi/1000)^2/(1-L), \quad (7)$$

where P is the required laser power in Watts, n is the number of irradiated spots, α is the corneal absorption coefficient in cm$^{-1}$, φ is the spot diameter in μm, and L is the loss (due to optics or other factors).

As an example, if a longer wavelength continuous wave thulium fiber laser is used for which α=25 cm$^{-1}$ and if a set of n=4 spots of φ=600 μm diameter is irradiated through optics with a loss L=0.2, the laser power required may be P=5.4W. As another example, if a longer wavelength continuous wave thulium fiber laser is used for which α=100 cm$^{-1}$ and if a set of n=8 spots of φ=500 μm diameter is irradiated with a loss L=0.3, the laser power required could be P=2.14W. For the first example, this illustrates that increased laser power may be required to use a longer wavelength (approximately 2.1 μm) continuous wave laser for which the absorption coefficient is approximately α=25 cm$^{-1}$ in order to irradiate even four spots with similar diameter as is currently used in pulsed Ho:YAG LTK treatments. For the second example, this illustrates that irradiating eight spots with a moderately powerful continuous wave laser at the optimal wavelength (from the standpoint of largest absorption coefficient) may involve using quite small diameter spots. However, using smaller diameter spots may lead to decreased efficiency since the radial heat loss due to thermal diffusion may be a much larger fraction of the total deposited laser energy than in the case of 1 mm diameter spots. Based on this, in particular embodiments, a 3W laser 106 operating at an optimal wavelength of approximately 1.94 μm is used to produce a four-beam array of irradiated spots with diameters in the 600 μm to 800 μm range.

The above description has described the use of the protective corneal applanator device 102 and the beam splitting systems 900, 950 in particular systems and for particular applications (such as LTK procedures). However, the protective corneal applanator device 102 may be used in any system and with any suitable ophthalmological procedure. Also, the beam splitting systems 900, 950 could be used in any other system, whether or not that system is used as part of an ophthalmological procedure. Further, the above description has often described the use of particular lasers operating at particular wavelengths, irradiance levels, durations, geometries, and doses. Any other suitable laser or non-laser light source(s) may be used during an ophthalmological procedure, and the light source(s) may operate using any suitable parameters. In addition, the above description has often referred to particular temperatures and temperature ranges. These temperatures and temperature ranges may vary depending on the circumstances, such as the temperature of a room in which a patient or the protective corneal applanator device 102 is located.

As noted above, to reshape a cornea using LTK or another procedure, it may be desirable to use one or more ocular/ophthalmic solutions that are deuterated. A deuterated ocular/ophthalmic solution may represent an aqueous solution in which deuterated water ($D_2O$) is substituted for normal protonated water ($H_2O$). For example, an aqueous sterile solution of 0.5% proparacaine hydrochloride ("proparacaine") in normal protonated water, typically packaged with a preservative (such as 0.01% benzalkonium chloride), can be used as a topical anesthetic on a patient's eye. However, proparacaine often causes corneal epithelial swelling, possibly up to twice the normal epithelial thickness or more. This would alter the dosimetry of LTK treatment because the thickened epithelium reduces laser energy reaching the corneal stroma (where thermal modification ideally occurs).

Substantial benefits may result from the application of proparacaine in deuterated water rather than normal protonated water. For example, deuterated water may have a much lower absorption coefficient than ordinary water at the Ho:YAG laser wavelength of 2.13 μm. As a result, if proparacaine is dissolved in $D_2O$, the swelling of the corneal epithelium may lead to a mixture of $D_2O$, HDO (monodeuterated water), and $H_2O$ that is less absorptive than $H_2O$ alone. Note that $D_2O$ and $H_2O$ may rapidly exchange protons and deuterons to yield an equilibrium mixture of all three water species, including HDO. The exact concentrations of all three species may depend on the concentrations of $H_2O$ and $D_2O$, which are time-dependent since $D_2O$ diffuses through the corneal epithelium from the anterior cells down to the basal cells and the epithelial basement membrane.

Since the heat capacity of the equilibrium mixture of all three water species may essentially be the same compared to normal protonated water, the lowered absorption may produce a cooler epithelium than for pure $H_2O$. This may protect the epithelium during LTK or other surgical eye procedures. Similarly, using a balanced saline solution (BSS) prepared from $D_2O$ may have a protective effect if the deuterated BSS is partly absorbed by the epithelium and/or if residual BSS remains on the corneal surface during treatment.

Figure 12:
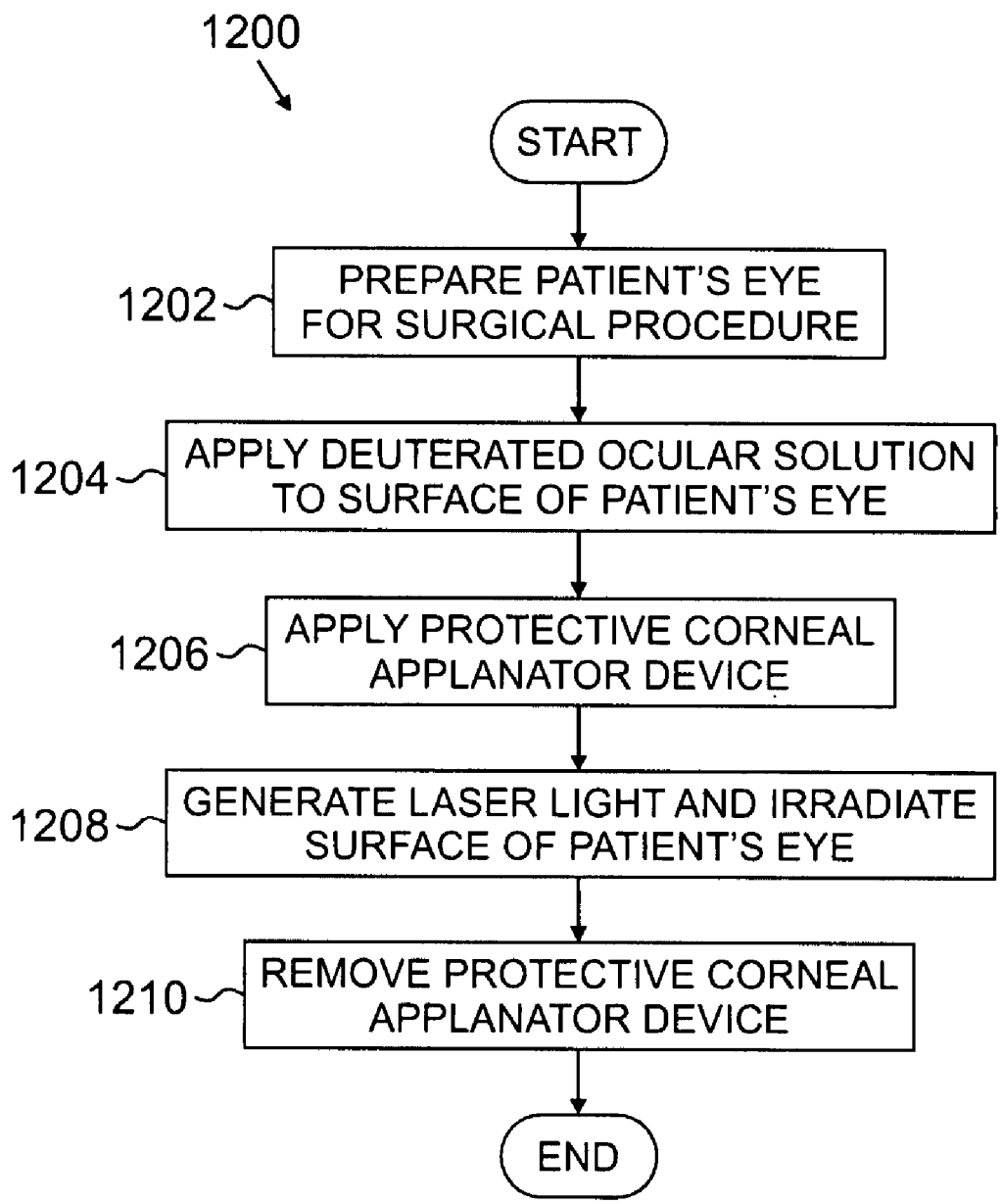
FIG. 12 illustrates an example method for using a deuterated ocular solution during a cornea reshaping procedure according to one embodiment of this disclosure.

FIG. 12 illustrates an example method 1200 for using a deuterated ocular solution during a cornea reshaping procedure according to one embodiment of this disclosure. The embodiment of the method 1200 shown in FIG. 12 is for illustration only. Other embodiments of the method 1200 could be used without departing from the scope of this disclosure. Also, for ease of explanation, the method 1200 is described as involving the use of the protective corneal applanator device 102 within the system 100. The method 1200 could involve the use of any other or additional device or system.

A patient's eye is prepared for a surgical procedure at step 1202. This could include, for example, placing anesthetic drops or other medication or materials into the patient's eye. As part of this preparation, a deuterated ocular solution is applied to the patient's eye at step 1204. This could include, for example, applying proparacaine to the patient's eye, where the proparacaine partially or substantially includes deuterated water instead of protonated water.

A protective corneal applanator device is applied to the patient's eye at step 1206. This could include, for example, placing the protective corneal applanator device 102 on the patient's eye and securing the protective corneal applanator device 102 in place. This could also include pressing the transparent window 210 of the protective corneal applanator device 102 onto the patient's eye so that the patient's eye achieves a desired shape. Laser light is generated and used to irradiate the surface of the patient's eye at step 1208, and the protective corneal applanator device is removed from the patient's eye at step 1210.

In some embodiments, the combined use of the protective corneal applanator device 102 (with passive or active cooling) and a deuterated ocular/ophthalmic solution may provide a greater level of epithelial protection during a surgical eye procedure. For example, their combined use may provide greater epithelial protection for a given level of laser irradiation. Moreover, their combined use may allow higher levels of laser irradiation to be used during the surgical procedure. These higher levels of laser irradiation could produce larger corneal shape changes in a patient's eye without causing a clinically significant wound healing response in the patient's eye.

In particular embodiments, disposable, single-use deuterated ocular solutions could be produced and used for LTK and other eye treatments. The use of disposable, single-use deuterated ocular solutions may provide certain benefits because conventional proparacaine often suffers from various problems that may affect LTK and other surgical eye procedures. For example, proparacaine itself is often manufactured with a huge variation in pH, which should be controlled to reduce epithelial toxicity. Also, proparacaine is typically manufactured with too high of a concentration, which should be reduced to reduce epithelial toxicity. Further, proparacaine has storage problems in that it may lose potency when stored at room temperature for two weeks or more. Beyond that, deuterated proparacaine may be susceptible to exchange with normal atmospheric water, leading to loss of deuteration. In addition, benzalkonium chloride, the preservative typically used with proparacaine, can cause epithelial injury.

For these reasons, single-use, sterilized, sealed containers of proparacaine could be used. These containers could be small, such as containers with approximately 1 milliliter volume, and could be carefully controlled with respect to concentration, pH, deuteration, and sterilization (without added preservative). The containers could be shipped to physicians or other personnel in refrigerated containers with instructions to refrigerate the contents until treatment. Proparacaine samples could also be packaged in a kit that contains pH test paper, deuterated BSS, and other accessories (such as a single-use sterilized contact lens) in the kit.

As noted above, the various systems, apparatuses, and methods described above could be modified to support the use of deuterated ocular solutions. For example, the systems and apparatuses could be modified to include a component for dispensing a deuterated ocular solution onto a patient's eye (such as from the reservoir 224). Also, the methods could be modified to include the placement of a deuterated ocular solution in a patient's eye.

It will be understood by those skilled in the art that many modifications and embodiments other than those listed above are possible without departing from the basic concept (i.e. using one or more deuterated ocular solutions and possibly one or more accessories for improving the predictability and stability of corneal shape changes suitable for vision correction during LTK or other procedures). It will also be understood that this has inherent differences from prior techniques in which an energy absorption modifier is applied to the epidermis of the skin or the epithelium of the cornea in order to provide epidermal or epithelial protection. Here, proparacaine actually causes epithelial swelling in which the corneal epithelial thickness is increased by the addition of deuterated water.

Although FIG. 12 illustrates one example of a method 1200 for using a deuterated ocular solution during a cornea reshaping procedure, various changes may be made to FIG. 12. For example, any other or additional steps could occur during a surgical eye procedure.

It may be advantageous to set forth definitions of certain words and phrases used in this patent document. The terms "include" and "comprise," as well as derivatives thereof, mean inclusion without limitation. The term "or" is inclusive, meaning and/or. The term "each" refers to every of at least a subset of the identified items. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. The term "controller" means any device, system, or part thereof that controls at least one operation. A controller may be implemented in hardware, firmware, or software, or a combination of at least two of the same. It should be noted that the functionality associated with any particular controller may be centralized or distributed, whether locally or remotely.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A method comprising:
    applying a deuterated ocular solution to an eye, the eye comprising a cornea, the deuterated ocular solution comprising deuterated water and one or more ocular drugs, the one or more ocular drugs causing swelling of a corneal epithelium in the cornea;
    applying a device to the cornea of the eye, the device comprising a window configured to contact at least a portion of the cornea; and
    irradiating at least part of the cornea to modify a stroma in the cornea using light energy that passes through the window and through the corneal epithelium during a cornea reshaping procedure, the window substantially transparent to the light energy.

2. The method of claim 1, wherein the one or more ocular drugs comprise proparacaine.

3. The method of claim 1, further comprising:
preventing, using the window and the deuterated ocular solution, clinically significant damage to the corneal epithelium of the cornea during the cornea reshaping procedure.

4. The method of claim 3, wherein preventing clinically significant damage to the corneal epithelium comprises preventing a temperature of the corneal epithelium from exceeding approximately 70° C during the cornea reshaping procedure.

5. The method of claim 1, further comprising:
maintaining at least a portion of the cornea at a desired initial temperature prior to irradiation of the cornea.

6. The method of claim 1, further comprising:
causing at least a portion of the cornea to have a desired shape using the window prior to irradiation of the cornea.

7. The method of claim 6, wherein the desired shape is substantially equal to at least one desired final radius of curvature of the cornea.

8. The method of claim 1, further comprising:
coupling the device to a fiber optic holder, the device comprising a first magnet configured to attract a second magnet in the fiber optic holder.

9. The method of claim 1, further comprising: generating the light energy using a continuous wave laser.

10. The method of claim 1, wherein a mixture of deuterated water, monodeuterated water, and protonated water forms in the coeal epithelium, the mixture having a lower absorption coefficient compared to protonated water such that an effect of the swelling on a dosimetry of the light energy is reduced.

* * * * *

UNITED STATES PATENT AND TRADEMARK OFFICE
CERTIFICATE OF CORRECTION

| | | |
|---|---|---|
| PATENT NO. | : 7,691,099 B2 | |
| APPLICATION NO. | : 11/825816 | |
| DATED | : April 6, 2010 | |
| INVENTOR(S) | : Michael J. Berry | |

It is certified that error appears in the above-identified patent and that said Letters Patent is hereby corrected as shown below:

Column 30, claim 10, line 16, delete "coeal" and replace with --corneal--.

Signed and Sealed this
Eighth Day of March, 2011

David J. Kappos
*Director of the United States Patent and Trademark Office*